United States Patent
Scialla et al.

(10) Patent No.: US 10,640,736 B2
(45) Date of Patent: *May 5, 2020

(54) CLEANING COMPOSITIONS COMPRISING ALKOXYLATED ESTERAMINES

(71) Applicant: The Procter & Gamble Company, Cincinnati, OH (US)

(72) Inventors: Stefano Scialla, Strombeek Bever (BE); Michelle Jackson, NewCastle Upon Tyne (GB); Bjoern Ludolph, Ludwigshafen (DE); Sophia Rosa Ebert, Mannheim (DE); Christian Bittner, Bensheim (DE); Frank Hulskotter, Bad Duerkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 84 days.

This patent is subject to a terminal disclaimer.

(21) Appl. No.: 16/028,453

(22) Filed: Jul. 6, 2018

(65) Prior Publication Data
US 2019/0010425 A1 Jan. 10, 2019

Related U.S. Application Data

(60) Provisional application No. 62/529,510, filed on Jul. 7, 2017, provisional application No. 62/594,599, filed on Dec. 5, 2017.

(51) Int. Cl.
*C11D 3/30* (2006.01)
*C07C 229/08* (2006.01)
*C11D 3/34* (2006.01)
*C11D 11/00* (2006.01)
*C11D 3/33* (2006.01)

(52) U.S. Cl.
CPC ............. *C11D 3/30* (2013.01); *C07C 229/08* (2013.01); *C11D 3/33* (2013.01); *C11D 3/3409* (2013.01); *C11D 11/0017* (2013.01)

(58) Field of Classification Search
CPC ............................ C11D 3/0036; C08G 73/00
USPC .......................................... 510/300; 528/422
See application file for complete search history.

(56) References Cited

U.S. PATENT DOCUMENTS 5,747,108 A    5/1998 Farooq et al.

FOREIGN PATENT DOCUMENTS

EP    0309052 A2    3/1989

OTHER PUBLICATIONS

International Search Report; International Application No. PCT/US2018/041013; dated Sep. 20, 2018; 15 pages.
Maria Rosa Infante: "Amino acid-based surfactants—ScienceDirect", C.R. Chimie 7 (Jun. 8, 2004), pp. 583-592, XP055506074, DOI: 10.1016/j.crci.2004.02.009; Retrieved from the internet: URL:https://www.sciencedirect.com/science/article/pii/S163107480400116X [retrieved on Sep. 11, 2018] figures Scheme 2, 3; table 1 p. 585-p. 587.

*Primary Examiner* — Khanh T Nguyen
(74) *Attorney, Agent, or Firm* — Melissa G. Krasovec

(57) ABSTRACT

Cleaning compositions that include alkoxylated esteramines. Related methods of preparation and use.

20 Claims, No Drawings

CLEANING COMPOSITIONS COMPRISING ALKOXYLATED ESTERAMINES

FIELD OF THE INVENTION

The present disclosure relates to cleaning compositions that include alkoxylated esteramines. The present disclosure also relates to methods of preparation and use of such compositions.

BACKGROUND OF THE INVENTION

Due to the increasing popularity of easy-care fabrics made of synthetic fibers as well as the increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even in cold water. To achieve satisfactory washing result at such low temperatures, i.e. results comparable to those obtained with hot water washes, the demands on low temperature detergents are especially high.

Greasy stains, such as those resulting from bacon or butter, are often quite challenging to remove, particularly at lower temperatures. It is known to include certain additives in detergent compositions to enhance the detergent power of conventional surfactants so as to improve the removal of grease stains at temperatures of 60° C. and below. Conventional cleaning compositions directed to grease removal frequently utilize various amine compounds which tend to show strong negative impacts on whiteness. As a consequence, there is still a continual need for compounds, particularly amine compounds, that provide grease removal abilities from fabrics and other soiled materials which at the same time do not negatively impact clay cleaning abilities or whiteness. Thus, the search for suitable, effective, and/or improved additives is ongoing.

There is a need for improved cleaning compositions, particularly those that can remove grease stains and/or provide stain removal at low wash temperatures.

SUMMARY OF THE INVENTION

The present disclosure relates to cleaning compositions that include alkoxylated esteramines. For example, the present disclosure relates to cleaning compositions that include: from about 1% to about 70%, by weight of the composition, of a surfactant system; and from about 0.1% to about 10% of an esteramine according to Formula (I) and/or a salt thereof, as described in more detail below.

The present disclosure also relates to a cleaning composition that includes: from about 1% to about 70%, by weight of the composition, of a surfactant system; and from about 0.1% to about 10% of an esteramine obtainable by (a) reacting an alcohol according to Formula (III), as described in more detail below, with one or more $C_2$ to $C_{16}$ alkylene oxide, followed by (b) at least partial esterification of the alkoxylated alcohol with at least one compound selected from alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV) as described in more detail below, and salts thereof.

The present disclosure also relates to a method of pretreating or treating a soiled fabric, the method including the step of contacting the soiled fabric with a cleaning composition as described herein, preferably wherein the soiled fabric includes a greasy stain.

The present disclosure also relates to a use of the esteramine and/or salt thereof according to the present disclosure in cleaning compositions, preferably laundry compositions, for removal of stains, preferably removal of greasy stains, more preferably the removal of greasy stains in wash water having a temperature of 30° C. or less.

DETAILED DESCRIPTION OF THE INVENTION

The present disclosure relates to cleaning compositions, such as laundry detergent compositions, that include alkoxylated esteramines. The alkoxylated esteramines as described herein have been found to be surprisingly effective in providing stain removal benefits. In particular, the alkoxylated esteramines are effective at removing greasy stains, such as those caused by bacon grease, even at relatively low temperatures.

Without wishing to be bound by theory, it is believed that alkoxylated esteramines are able to increase the ability of surfactants to emulsify soil by decreasing the interfacial tension between grease and wash solution thanks to a co-surfactancy mechanism. This improves surfactant packing and, as a consequence, detergent efficiency.

The compositions and methods of the present disclosure are described in more detail below. Features and benefits of the various embodiments of the present invention will become apparent from the following description, which includes examples of specific embodiments intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein, the term "soiled material" is used non-specifically and may refer to any type of flexible material consisting of a network of natural or artificial fibers, including natural, artificial, and synthetic fibers, such as, but not limited to, cotton, linen, wool, polyester, nylon, silk, acrylic, and the like, as well as various blends and combinations. Soiled material may further refer to any type of hard surface, including natural, artificial, or synthetic surfaces, such as, but not limited to, tile, granite, grout, glass, composite, vinyl, hardwood, metal, cooking surfaces, plastic, and the like, as well as blends and combinations.

Generally, as used herein, the term "obtainable by" means that corresponding products do not necessarily have to be produced (i.e. obtained) by the corresponding method or process described in the respective specific context, but also products are comprised which exhibit all features of a product produced (obtained) by said corresponding method or process, wherein said products were actually not produced (obtained) by such method or process. However, the term "obtainable by" also comprises the more limiting term "obtained by", i.e. products which were actually produced (obtained) by a method or process described in the respective specific context.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cleaning Composition

As used herein the phrase "cleaning composition" includes compositions and formulations designed for cleaning soiled material and/or surfaces. Such compositions include but are not limited to, fabric care compositions, including laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, dish washing compositions, hard surface cleaning compositions, unit dose formulation, delayed delivery formulation, detergent contained on or in a porous substrate or nonwoven sheet, personal care compositions such as shampoos and body washes, and other suitable forms that may be apparent to one skilled in the art in view of the teachings herein. Such compositions may be used as a pre-laundering treatment, a post-laundering treatment, or may be added during the rinse or wash cycle of the laundering operation. The cleaning compositions may have a form selected from liquid, powder, single-phase or multi-phase unit dose article, film, woven web, non-woven web, dissolvable bead or lenticular particle, gel, paste, bar, or flake.

Alkoxylated Esteramines

The cleaning compositions described herein include alkoxylated esteramines and/or salts thereof. Such compounds may lead to improved cleaning performance of such compositions, for example of liquid laundry detergents, particularly when used in cold water washing conditions. In particular, it has been found that alkoxylated esteramines according to the present disclosure surprisingly boost grease cleaning performance of liquid laundry detergents, especially under cold water washing conditions. The alkoxylated esteramines of the present disclosure may also show improved compatibility in liquid laundry detergent formulations.

The cleaning compositions of the present disclosure may include from about 0.1% to about 10%, in some examples, from about 0.2% to about 5%, and in other examples, from about 0.5% to about 3%, by weight the composition, of an alkoxylated esteramine and/or salt thereof.

The alkoxylated esteramines may include esteramines of Formula (I) and salts thereof,

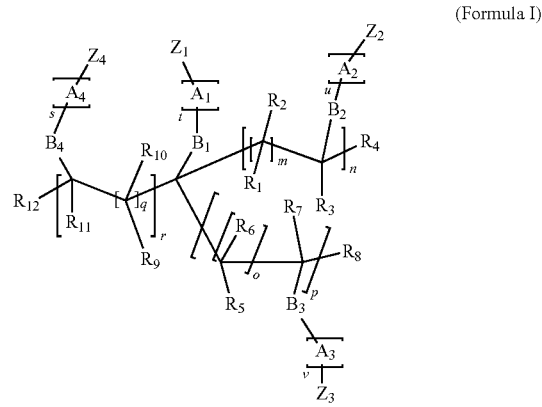

(Formula I)

wherein independently from each other
n being an integer from 0 to 12,
m being an integer for each repetition unit n independently selected from 0 to 12;
p being an integer from 0 to 12,
o being an integer for each repetition unit p independently selected from 0 to 12;
r being an integer from 0 to 12,
q being an integer for each repetition unit r independently selected from 0 to 12;
s being an integer from 0 to 100;
t being an integer from 1 to 100;
u being an integer from 0 to 100;
v being an integer from 0 to 100;
with the sum of s, t, u, and v being equal to or greater than 1;
$A_1$, $A_2$, $A_3$, and $A_4$ are independently from each other and independently for each repetition unit s, t, u, or v, selected from the list consisting of ethyleneoxy group, propyleneoxy group (e.g., 1,2-propyleneoxy and/or isopropyleneoxy group), 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein when s, t, u, and/or v equal to or greater than 1, the oxygen atom of the first $A_1$, $A_2$, $A_3$, and $A_4$ group is bound to the B group and the subsequent $A_1$, $A_2$, $A_3$, and $A_4$ groups, when they exist, are bound via an oxygen atom to the previous $A_1$, $A_2$, $A_3$, and $A_4$ group;

$B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$R_1$, $R_2$, and $R_3$ being independently for each repetition unit o of each repetition unit p being selected from the group consisting of H, linear alkyl, branched alkyl, and cycloalkyl;

$R_5$, $R_6$, and $R_7$ being independently for each repetition unit m of each repetition unit n being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl; and wherein $Z_1$, $Z_2$, $Z_3$, and/or $Z_4$ are independently selected from the group consisting of —OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *,

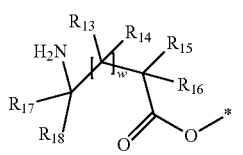

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl, with the proviso that at least one of $Z_1$, $Z_2$, $Z_3$, and/or $Z_4$ is present and is not —OH.

In the alkoxylated esteramines of the present disclosure, any of the $A_1$, $A_2$, $A_3$, and/or $A_4$ groups may independently be branched or linear.

In the alkoxylated esteramines of the present disclosure, it may be that when n, p, and r are equal to zero, $Z_1$ is selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the provisio of at least one group $R_4$, $R_8$, and/or $R_{12}$ containing at least 7 or more carbon atoms;

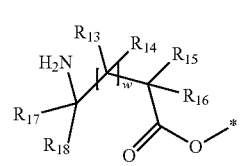

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl.

In the alkoxylated esteramines of the present disclosure, it may be that when p and r are both equal to 0, and n being at least 1, $Z_1$ and $Z_2$, are independently selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the provisio that at least one substituent $Z_1$ and/or $Z_2$ is not OH, and with the proviso that $R_3$ contains equal to or more than 2 carbon atoms.

In the alkoxylated esteramines of the present disclosure, it may be that when n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the proviso that at least one substituent $Z_1$, and/or $Z_2$, and/or $Z_3$, and/or $Z_4$, is not OH, and wherein for n and p equal to 1 and r equal to 0 at least one unit $A_1$, $A_2$, or $A_3$ is selected from the group consisting of ethyleneoxy group, propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group.

In the alkoxylated esteramines of the present disclosure, it may be that $A_1$, $A_2$, $A_3$, and $A_4$ are independently from each other, and independently for each repetition unit s, t, u, or v, selected from the list consisting of ethyleneoxy group, propyleneoxy group, 1,2-butyleneoxy group, 2,3-butyleneoxy group, i-butyleneoxy group pentenyloxy group, hexyloxy group, styryloxy group, decenyloxy group, dodecyloxy group, tetradecenyloxy group and hexadecenyloxy group, wherein for s, t, u, and/or v equal to 1 the oxygen atom of the $A_1$, $A_2$, $A_3$, and $A_4$ group is bound to the B group and the following $A_1$, $A_2$, $A_3$, and $A_4$ groups are always bound via the oxygen atom to the previous $A_1$, $A_2$, $A_3$, and $A_4$ group. When either of s, t, u, or v is equal to or more than 2, the independently selected $A_1$, $A_2$, $A_3$, and $A_4$ for each repetition unit s, t, u, or v either form a randomly distributed sidechain of various alkylenyloxy units for each sidechain s, t, u, or v, or the form a block structure with at least one alkylenyloxy group repeating itself at least two times, optionally followed by further blocks of different alkylenyloxy group repeating themselves at least two times.

In the alkoxylated esteramines of the present disclosure, it may be that $A_1$, $A_2$, $A_3$, and $A_4$ are independently from each other and independently for each repetition unit s, t, u, or v, selected from the list consisting of ethyleneoxy group, propyleneoxy group, and 1,2-butyleneoxy group. In another embodiment, $A_1$, $A_2$, $A_3$, and $A_4$ form each a block of at least two ethyleneoxy groups followed by a block of at least two propyleneoxy groups, optionally followed by another block of at least two ethyleneoxy groups. In another embodiment, $A_1$, $A_2$, $A_3$, and $A_4$ form each a block of at least two propyleneoxy groups followed by a block of at least two ethyleneoxy groups, optionally followed by another block of at least two propyleneoxy groups. In another embodiment, $A_1$, $A_2$, $A_3$, and $A_4$ are selected from the list consisting of ethyleneoxy group, propyleneoxy group, and 1,2-butyleneoxy group in such a way that at least one block of ethyleneoxy groups, propyleneoxy groups, or 1,2-butyleneoxy groups is formed, optionally followed by one or more blocks of ethyleneoxy groups, propyleneoxy groups, or 1,2-butyleneoxy groups. In another embodiment, $A_1$, $A_2$, $A_3$, and $A_4$ are ethyleneoxy groups. In another embodiment, $A_1$, $A_2$, $A_3$, and $A_4$ are propyleneoxy groups. In another embodiment, $A_1$, $A_2$, $A_3$, and $A_4$ are selected in such a way that at least for one of $A_1$, $A_2$, $A_3$, and $A_4$ a block of one to five ethyleneoxy groups is followed by a block of one to three propylenoxy groups followed by a block of one to five ethylenoxy groups.

In the alkoxylated esteramines of the present disclosure, it may be that s, u, or v are each individually in the range of from 0 to 50 and t in the range of from 1 to 50. In another embodiment, s, u, or v are each individually in the range of from 0 to 20 and t in the range of from 1 to 20.

In the alkoxylated esteramines of the present disclosure, it may be that $B_1$, $B_2$, $B_3$, and $B_4$ are independently from each other selected from the group consisting of a bond, and linear $C_1$ to $C_{12}$ alkanediyl groups. In another embodiment, $B_1$, $B_2$, $B_3$, and $B_4$ are independently from each other selected from the group consisting of a bond, and linear $C_1$ to $C_6$ alkanediyl groups. In another embodiment, $B_1$, $B_2$, $B_3$, and $B_4$ are independently from each other selected from the group consisting of a bond, and linear $C_1$ to $C_3$ alkanediyl groups. In another embodiment, $B_1$, $B_2$, $B_3$, and $B_4$ are independently from each other selected from the group consisting of a bond, and a $C_1$ alkanediyl group. In another embodiment $B_1$, $B_2$, $B_3$, and $B_4$ are all selected from the group consisting of a bond, and a $C_1$ alkanediyl group. In another embodiment $B_1$, $B_2$, $B_3$, and $B_4$ are all a bond.

In the alkoxylated esteramines of the present disclosure, it may be that $R_1$, $R_2$, $R_3$, $R_4$, $R_5$, $R_6$, $R_7$, $R_8$, $R_9$, $R_{10}$, $R_{11}$, and $R_{12}$ are all independently selected from the group consisting of H, linear alkyl, branched alkyl, and cycloalkyl. In one embodiment, $R_1$, $R_2$, $R_3$, $R_4$, $R_5$, $R_6$, $R_7$, $R_8$, $R_9$, $R_{10}$, $R_{11}$, and $R_{12}$ are all independently selected from the group consisting of H, linear $C_1$ to $C_{12}$ alkyl, and $C_1$ to $C_{12}$ branched alkyl. In another embodiment, $R_1$, $R_2$, $R_3$, $R_4$, $R_5$, $R_6$, $R_7$, $R_8$, $R_9$, $R_{10}$, $R_{11}$, and $R_{12}$ are all independently selected from the group consisting of H, linear $C_1$ to $C_6$ alkyl, and $C_1$ to $C_9$ branched alkyl.

In the alkoxylated esteramines of the present disclosure, it may be that for any one $Z_1$, $Z_2$, $Z_3$, and $Z_4$ being selected a compound according to Formula (II), said compound according to Formula (II) connects to the compound of Formula (I) via the bond labeled with *.

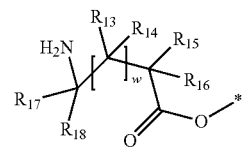

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl. In one embodiment of the present invention, $R_{13}$, $R_{14}$, $R_{15}$, $R_{16}$, $R_{17}$, and $R_{18}$ are all independently selected from the group consisting of H, linear $C_1$ to $C_{12}$ alkyl, and $C_1$ to $C_{12}$ branched alkyl. In another embodiment, $R_{13}$, $R_{14}$, $R_{15}$, $R_{16}$, $R_{17}$, and $R_{18}$ are all independently selected from the group consisting of H, linear $C_1$ to $C_6$ alkyl, and $C_1$ to $C_9$ branched alkyl.

In the alkoxylated esteramines of the present disclosure, it may be that n, p, and r are equal to zero (0) and $Z_1$ is selected from the group consisting of alanine, glycine, lysine, and of compounds according to Formula (II), wherein w is an integer in the range of from 1 to 4, and the compound according to Formula (II) connects to the compound according to Formula (I) via the bond labeled with *, with the provisio of at least one group $R_4$, $R_8$, and/or $R_{12}$ containing at least 7 or more carbon atom. It may be that n, p, and r are equal to zero (0) and $Z_1$ is alanine. It may be that n, p, and r are equal to zero (0) and $Z_1$ is a compound according to Formula (II) with w=0 and $R_{15}$ to $R_{18}$ are all H. It may be that n, p, and r are equal to zero (0) and $Z_1$ is a compound according to Formula (II) with w=1 and $R_{13}$ to $R_{18}$ are all H. It may be that n, p, and r are equal to zero (0) and $Z_1$ is a compound according to Formula (II) with w=3 and $R_{13}$ to $R_{18}$ are all H.

In the alkoxylated esteramines of the present disclosure, it may be that n, p, and r are equal to zero (0) and $B_1$ is selected from branched or linear $C_1$- to $C_{12}$-alkyl and $R_8$ is selected from linear or branched $C_6$- to $C_{23}$-alkyl. It may be that n, p, and r are equal to zero (0) and $B_1$ is selected from branched or linear $C_1$- to $C_{12}$-alkyl and $R_8$ is selected from linear or branched $C_1$- to $C_3$-alkyl. It may be that n, p, and r being equal to zero (0) and $B_1$ being 2-ethyl-ethandiyl and $R_8$ being linear $C_3$-alkyl.

In the alkoxylated esteramines of the present disclosure, it may be that n, p, and r are equal to zero (0), and $B_1$ is selected from branched or linear $C_1$- to $C_{12}$-alkyl and $R_8$ is selected from linear or branched $C_1$- to $C_3$-alkyl, and $Z_1$ is a is a compound according to Formula (II) with w=3 and $R_{13}$ to $R_{18}$ are all H.

In the alkoxylated esteramines of the present disclosure, it may be that n, p, and r are equal to zero (0), and $B_1$ is selected from branched or linear $C_6$- to $C_{12}$-alkyl and $R_8$ is selected from linear or branched $C_1$- to $C_3$-alkyl, t is in the range of from 1 to 10, $A_1$ is for each repetition unit t ethyleneoxy group, and $Z_1$ is selected from the group consisting of alanine, a compound according to Formula (II) with w=0 and $R_{15}$ to $R_{18}$ all H, a compound according to Formula (II) with w=1 and $R_{13}$ to $R_{18}$ all H, and a compound according to Formula (II) with w=3 and $R_{13}$ to $R_{18}$ all H.

In the alkoxylated esteramines of the present disclosure, it may be that n, p, and r are equal to zero (0), and $B_1$ is selected from branched or linear $C_6$- to $C_{12}$-alkyl and $R_8$ is selected from linear or branched $C_1$- to $C_3$-alkyl, $R_4$ and $R_{12}$ are selected from H and linear or branched $C_1$- to $C_3$-alkyl, t is in the range of from 1 to 10, $A_1$ is for each repetition unit t propyleneoxy group, and $Z_1$ is selected from the group consisting of alanine, a compound according to Formula (II) with w=0 and $R_{15}$ to $R_{18}$ all H, a compound according to Formula (II) with w=1 and $R_{13}$ to $R_{18}$ all H, and a compound according to Formula (II) with w=3 and $R_{13}$ to $R_{18}$ all H.

In the alkoxylated esteramines of the present disclosure, it may be that p and r are both equal to 0, and n being at least 1, $Z_1$ and $Z_2$, are independently selected from the group consisting of OH, alanine, glycine, lysine, and a compound according to Formula (II), wherein w is an integer in the range of from 1 to 4, wherein said compound according to Formula (II) connects to the compound according to Formula (I) via the bond labeled with *, with the provisio that at least one substituent $Z_1$ and/or $Z_2$ is not H, and with the provisio that $R_3$ contains equal to or more than 2 carbon atoms. It may be that p and r are both equal to 0, and n being at least 1, $Z_1$ and $Z_2$, are independently selected from the group consisting of alanine, a compound according to Formula (II), wherein w=0 and $R_{15}$ to $R_{18}$ are all H, a compound according to Formula (II), wherein w=1 and $R_{13}$ to $R_{18}$ are all H, and a compound according to Formula (II), wherein w=3 and $R_{13}$ to $R_{18}$ are all H, wherein said compound according to Formula (II) connects to the compound according to Formula (I) via the bond labeled with *, with the provisio that at least one substituent $Z_1$ and/or $Z_2$ is not H, and with the provisio that $R_3$ contains equal to or more than 2 carbon atoms.

In the alkoxylated esteramines of the present disclosure, it may be that p and r are both equal to 0, and n being 1, with m being in the range of from 0 to 10, with $R_8$ and $R_{12}$ being H. In another embodiment of the present invention, p and r are both equal to 0, and n being 1, with m being in the range of from 0 to 5, with $R_8$ and $R_{12}$ being H. In one embodiment, p and r are both equal to 0, and n being at least 1, wherein m is equal to 1 and $R_1$ and $R_2$ are both linear $C_2$ to $C_4$ alkyl groups. It may be that p and r are both equal to 0, and n being 1, with m being in the range of from 0 to 1, with $R_8$ and $R_{12}$ being H and $B_1$ and $B_2$ being bonds. In another embodiment of the present invention, p and r are both equal to 0, and n being 1, with m being 1, $R_3$, $R_4$, $R_8$ and $R_{12}$ being H, $R_1$ and $R_2$ being methyl, and $B_1$ and $B_2$ being bonds. In another embodiment of the present invention, p and r are both equal to 0, and n being 1, with m being 1, $R_3$, $R_4$, $R_8$ and $R_{12}$ being H, $R_1$ being butyl, $R_2$ being ethyl, and $B_1$ and $B_2$ being bonds. It may be that p and r are both equal to 0, and n being 1, with m being 1, $R_3$, $R_4$, $R_8$ and $R_{12}$ being H, $R_1$ being methyl, $R_2$ being propyl, and $B_1$ and $B_2$ being bonds. It may be that p and r are both equal to 0, and n being 1, with m being 1, $R_4$ being propyl, $R_3$, $R_8$ and $R_{12}$ being H, $R_1$ being H, $R_2$ being ethyl, and $B_1$ and $B_2$ being bonds. It may be that p and r are both equal to 0, and n being 5, with m being 0, with $R_1$, $R_2$, $R_4$, $R_8$ and $R_{12}$ being H and $B_1$ and $B_2$ being bonds.

In the alkoxylated esteramines of the present disclosure, it may be that p and r are both equal to 0, and n being 1, with m being in the range of from 0 to 10, with $R_8$ and $R_{12}$ being H, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups. It may be that p and r are both equal to 0, and n being 1, with m being in the range of from 0 to 5, with $R_8$ and $R_{12}$ being H, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups. It may be that p and r are both equal to 0, and n being at least 1, wherein m is equal to 1 and $R_1$ and $R_2$ are both linear $C_2$ to $C_4$ alkyl groups, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups. It may be that p and r are both equal to 0, and n being 1, with m being in the range of from 0 to 1, with $R_8$ and $R_{12}$ being H, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups. In another embodiment of the present invention, p and r are both equal to 0, and n being 1, with m being 1, $R_3$, $R_4$, $R_8$ and $R_{12}$ being H, and $R_1$ and $R_2$ being methyl, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups. It may be that p and r are both equal to 0, and n being 1, with m being 1, $R_3$, $R_4$, $R_8$ and $R_{12}$ being H, and $R_1$ being butyl and $R_2$ being ethyl, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, and $B_1$ and $B_2$ being bonds. It may be that p and r are both equal to 0, and n being 1, with m being 1, $R_3$, $R_4$, $R_8$ and $R_{12}$ being H, and $R_1$ being methyl and $R_2$ being propyl, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, and $B_1$ and $B_2$ being bonds. It may be that p and r are both equal to 0, and n being 1, with m being 1, $R_3$, $R_4$, $R_8$ and $R_{12}$ being H, and $R_1$ being methyl and $R_2$ being propyl, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, and $B_1$ and $B_2$ being bonds. It may be that p and r are both equal to 0, and n being 1, with m being 1, $R_4$ being propyl, $R_3$, $R_8$ and $R_{12}$ being H, and $R_1$ being H and $R_2$ being ethyl, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, and $B_1$ and $B_2$ being bonds. It may be that p and r are both equal to 0, and n being 5, with m being 0, with $R_3$, $R_4$, $R_8$ and $R_{12}$ being H, t is of from 1 to 10, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, and $B_1$ and $B_2$ being bonds.

In the alkoxylated esteramines of the present disclosure, it may be that n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of OH, alanine, glycine, lysine and Formula (II), wherein w is an integer in the range of from 1 to 4, wherein Formula (II) connects to Formula (I) via the bond labeled with *, with the provisio that at least one substituent $Z_1$, and/or $Z_2$, and/or $Z_3$, and/or $Z_4$, is not OH. It may be that n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of alanine, a compound according to Formula (II), wherein w=0 and $R_{15}$ to $R_{18}$ are all H, a compound according to Formula (II), wherein w=1 and $R_{13}$ to $R_{18}$ are all H, and a compound according to Formula (II), wherein w=3 and $R_{13}$ to $R_{18}$ are all H, wherein said compound according to Formula (II) connects to the compound according to Formula (I) via the bond labeled with *, and wherein for n and p equal to 1 and r equal to 0 at least one unit $A_1$, $A_2$, or $A_3$ is selected from the group consisting of ethyleneoxy group, propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group.

In the alkoxylated esteramines of the present disclosure, it may be that n and p are both equal to 1, r is equal to 0, m and o are both equal to 0, $B_1$, $B_2$, and $B_3$ are equal to a chemical bond, $R_3$, $R_4$, $R_7$, $R_8$, and $R_{12}$ are all equal to H. It may be that n and p are both equal to 1, r is equal to 0, m and o are both equal to 0, $B_1$, $B_2$, and $B_3$ are equal to methanediyl, $R_3$, $R_4$, $R_7$, and $R_8$, are all equal to H, and $R_{12}$ is equal to ethyl. In one embodiment, n and p are both equal to 1, r is equal to 0, m and o are equal to 0, $R_4$, $R_8$, and $R_{12}$ are equal to H. It may be that n and p are both equal to 1, r is equal to 0, m and o are equal to 0, $R_4$, $R_8$, and $R_{12}$ are equal to H, and $B_1$, $B_2$, and $B_3$ are all bonds. It may be that n and p are both equal to 1, r is equal to 0, m and o are equal to 1, $R_1$, $R_2$, $R_3$, $R_4$, $R_8$, $R_6$, $R_7$, and $R_8$ are all H, $R_{12}$ is ethyl, and $B_1$, $B_2$, and $B_3$ are all bonds. It may be that n, p and r are all equal to 1, m, o, and q are 1, $R_1$, $R_2$, $R_3$, $R_4$, $R_5$, $R_6$, $R_7$, $R_8$, $R_9$, $R_{10}$, $R_{11}$, $R_{12}$ are all H, and $B_1$, $B_2$, $B_3$, and $B_4$ are all bonds.

In the alkoxylated esteramines of the present disclosure, it may be that n and p are both equal to 1, r is equal to 0, m and o are both equal to 0, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, $A_3$ is for each repetition unit v selected from the group consisting of ethyleneoxy groups and propyleneoxy groups, $B_1$, $B_2$, and $B_3$ are equal to a chemical bond, $R_3$, $R_4$, $R_7$, $R_8$, and $R_{12}$ are all equal to H. It may be that n and p are both equal to 1, r is equal to 0, m and o are both equal to 0, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, $A_3$ is for each repetition unit v selected from the group consisting of ethyleneoxy groups and propyleneoxy groups, $B_1$ is equal to methanediyl, $B_2$, and $B_3$ are equal to a chemical bond, $R_3$, $R_4$, $R_7$, and $R_8$, are all equal to H, and $R_{12}$ is equal to ethyl. In one embodiment, n and p are both equal to 1, r is equal to 0, m and o are equal to 0, $R_4$, $R_8$, and $R_{12}$ are equal to H. It may be that n and p are both equal to 1, r is equal to 0, m and o are equal to 0, $R_4$, $R_8$, and $R_{12}$ are equal to H, $A_1$ is for each repetition unit t selected from the group consisting of ethyleneoxy groups and propyleneoxy groups, u is of from 1 to 10, and $A_2$ is for each repetition unit u selected from the group consisting of ethyleneoxy groups and propyleneoxy groups, $A_3$ is for each repetition unit v selected from the group consisting of ethyleneoxy groups and propyleneoxy groups, and $B_1$, $B_2$, and $B_3$ are all bonds. It may be that n and p are both equal to 1, r is equal to 0, m and o are equal to 1, $R_1$, $R_2$, $R_3$, $R_4$, $R_5$, $R_6$, $R_7$, and $R_8$ are all H, $R_{12}$ is ethyl, and $B_1$, $B_2$, and $B_3$ are all bonds. In another embodiment, n, p and r are all equal to 1, m, o, and q are 1, $R_1$, $R_2$, $R_3$, $R_4$, $R_5$, $R_6$, $R_7$, $R_8$, $R_9$, $R_{10}$, $R_{11}$, $R_{12}$ are all H, Au is for each repetition unit t selected from the group consisting of ethyleneoxy groups and propyleneoxy groups, u is of from 1 to 10, $A_2$ is for each repetition unit u selected from the group consisting of ethyleneoxy groups and propyleneoxy groups, $A_3$ is for each repetition unit v selected from the group consisting of ethyleneoxy groups and propyleneoxy groups, $A_4$ is for each repetition unit s selected from the group consisting of ethyleneoxy groups and propyleneoxy groups, and $B_1$, $B_2$, $B_3$, and $B_4$ are all bonds.

The esteramines of the present invention may be obtained either as free amines, as salts thereof or as a mixture of free amines and salts. Salts may be formed by at least partial protonation of the amine groups by an acid being a protic organic acid or a protic inorganic acid. The acid for at least partial protonation of the amine groups may be selected from the group consisting of methanesulfonic acid, hydrochloric acid, hydrobromic acid, sulfuric acid, phosphoric acid, toluene sulfonic acid, citric acid, lactic acid, $C_{12}$-$C_{18}$ fatty acid, alkyl benzene sulfonic acids, alkyl sulphonic acids, alkyl sulfate acids, alkyl ethyoxysulfate acids, alkoxylated or non-alkoxylated copolymers of acrylic acid and maleic acid, and mixtures thereof. The acid may be selected from the group of methanesulfonic acid, hydrochloric acid, and sulfuric acid. The acid may be methanesulfonic acid.

Partial protonation may be protonation of the amine groups in the range of from 1 to 99 mol-% of all amine groups, or in the range of from 10 to 90 mol-% of all amine groups, or in the range of from 25 to 85 mol-%, or in the range of from 40 to 75 mol-% of all amine groups.

The present disclosure also contemplates combinations of at least two (different) esteramines as presented herein. The present disclosure also relates to combinations of the embodiments described above in combination with similar, but non-alkoxylated, compounds, e.g., non-alkoxylated esteramines. These compounds may be present in low amounts, e.g., less than about 5% by weight of the total esteramines present in the composition.

It is recognized that the alkoxylated esteramines of the present disclosure may be asymmetrically alkoxylated, meaning that the degree of alkoxylation may not be the same in each portion of the compound. Put another way, when at least two of s, t, u, and v are at least 1, the at least two of s, t, u, and v may not be equal to each other in a given compound.

Esteramines or salts thereof may be prepared by a process comprising the following steps. An alcohol may be alkoxylated with one or more $C_2$ to $C_{16}$ alkylene oxide, followed by esterification, as described in more detail below.

a) Alkoxylation. An alcohol of Formula (III)

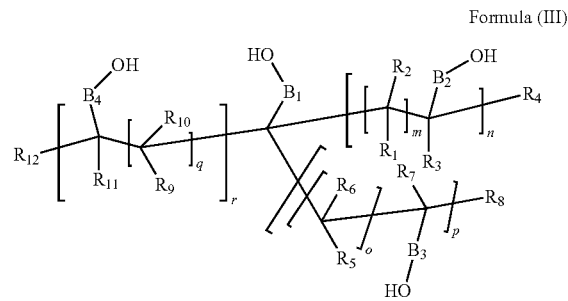

Formula (III)

wherein independently from each other
n being an integer from 0 to 12,
m being an integer for each repetition unit n independently selected from 0 to 12;
p being an integer from 0 to 12, o being an integer for each repetition unit p independently selected from 0 to 12;

r being an integer from 0 to 12, q being an integer for each repetition unit r independently selected from 0 to 12;

$B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$R_1$, $R_2$, and $R_3$ being independently for each repetition unit o of each repetition unit p being selected from the group consisting of H, linear alkyl, branched alkyl, and cycloalkyl;

$R_5$, $R_6$, and $R_7$ being independently for each repetition unit m of each repetition unit n being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl; may be alkoxylated with one or more $C_2$ to $C_{16}$ alkylene oxide. The resulting alkoxylated alcohol may be esterified, as described in more detail below.

b) Esterification. The alkoxylated alcohol may be at least partially esterified with at least one acid selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and acids of Formula (IV)

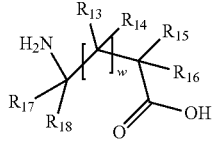

(Formula IV)

with w being an integer from 0 to 12, $R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

$B_1$, $B_2$, $B_3$, and $B_4$ may be independently from each other selected from the group consisting of a bond, and linear $C_1$ to $C_{12}$ alkanediyl groups. In another embodiment, $B_1$, $B_2$, $B_3$, and $B_4$ are independently from each other selected from the group consisting of a bond, and linear $C_1$ to $C_6$ alkanediyl groups. $B_1$, $B_2$, $B_3$, and $B_4$ may be independently from each other selected from the group consisting of a bond, and linear $C_1$ to $C_3$ alkanediyl groups. $B_1$, $B_2$, $B_3$, and $B_4$ may be independently from each other selected from the group consisting of a bond, and a $C_1$ alkanediyl group. $B_1$, $B_2$, $B_3$, and $B_4$ may be all selected from the group consisting of a bond, and a $C_1$ alkanediyl group. $B_1$, $B_2$, $B_3$, and $B_4$ may all be a bond.

$R_1$, $R_2$, $R_3$, $R_4$, $R_5$, $R_6$, $R_7$, $R_8$, $R_9$, $R_{10}$, $R_{11}$, and $R_{12}$ may all be independently selected from the group consisting of H, linear alkyl, branched alkyl, and cycloalkyl. $R_1$, $R_2$, $R_3$, $R_4$, $R_5$, $R_6$, $R_7$, $R_8$, $R_9$, $R_{10}$, $R_{11}$, and $R_{12}$ may all be independently selected from the group consisting of H, linear $C_1$ to $C_{12}$ alkyl, and $C_1$ to $C_{12}$ branched alkyl. $R_1$, $R_2$, $R_3$, $R_4$, $R_5$, $R_6$, $R_7$, $R_8$, $R_9$, $R_{10}$, $R_{11}$, and $R_{12}$ may all be independently selected from the group consisting of H, linear $C_1$ to $C_6$ alkyl, and $C_1$ to $C_9$ branched alkyl.

An alkoxylated esteramine may be obtained according to the following process.

Step a) Alkoxylation of alcohol according to Formula (III) with at least one $C_2$- to $C_{16}$-akylene oxide.

The alcohol of Formula (III) may be reacted with one single $C_2$- to $C_{16}$-alkylene oxide or combinations of two or more different $C_2$- to $C_{16}$-alkylene oxides. Using two or more different $C_2$- to $C_{16}$-alkylene oxides, the resulting polymer can be obtained as a block-wise structure or a random structure.

The molar ratio of alcohol of Formula (III) to total alkylene oxide may be in the range of from 1:1 to 1:400. The molar ratio of the moles of hydroxyl groups of the alcohol of Formula (III) to the alkylene oxides with which the alkoxylation reaction is carried out may lie in the range of 1:1 to 1:100. The ratio of the moles of hydroxyl groups of the alcohol of Formula (III) to the alkylene oxides at which the alkoxylation reaction is carried out may lie in the range of from 1:2 to 1:50, in another embodiment in the range of 1:3 to 1:10.

This reaction may be undertaken generally in the presence of a catalyst at a reaction temperature from about 70 to about 200° C., or from about 80 to about 160° C. This reaction may be affected at a pressure of up to about 10 bar, or at a pressure of up to about 8 bar.

Examples of suitable catalysts comprise basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. Alkali metal hydroxides may be used. Potassium hydroxide and sodium hydroxide may be used. Typical use amounts for the base are from 0.01 to 10% by weight, in particular from 0.05 to 2% by weight, based on the total amount of alcohol and $C_2$- to $C_{16}$-alkylene oxide.

Step b) Esterification

The esterification reaction may be performed as known in the art. An inorganic or organic protic acid may be added to the product of step a). The molar ratio of amino acid to hydroxyl groups of the alkoxylated alcohol of step a) may be 0.8:1 to 1:1.5. The process may be carried out with the molar ratio of the acid to the hydroxyl groups of the alkoxylated alcohol of step a) being in the range of from 0.1:1 to 1:1. Reaction temperatures may be from 50° C. to 200° C., or from 80° C. to 160° C. The reaction may be affected by applying vacuum from 1000 mbar to 1 mbar, in another embodiment from 500 mbar to 5 mbar. Reaction times may be from 2 to 48 hours. Suitable solvents for the reaction may be water, toluene, and/or xylene.

Surfactant System

The cleaning compositions comprise a surfactant system in an amount sufficient to provide desired cleaning properties. In some embodiments, the cleaning composition comprises, by weight of the composition, from about 1% to about 70% of a surfactant system. In other embodiments, the liquid cleaning composition comprises, by weight of the composition, from about 2% to about 60% of the surfactant system. In further embodiments, the cleaning composition comprises, by weight of the composition, from about 5% to about 30% of the surfactant system. The surfactant system may comprise a detersive surfactant selected from anionic surfactants, nonionic surfactants, cationic surfactants, zwitterionic surfactants, amphoteric surfactants, ampholytic surfactants, and mixtures thereof. Those of ordinary skill in the art will understand that a detersive surfactant encompasses any surfactant or mixture of surfactants that provide cleaning, stain removing, or laundering benefit to soiled material.

Anionic Surfactant

The compositions of the present disclosure may comprise at least about 10%, or at least about 20%, or at least about 30%, or at least about 50%, or at least about 60%, or at least about 70% by weight of an anionic surfactant. The compositions of the present disclosure may comprise less than 100%, or less than 90%, or less than about 85%, or less than about 75%, or less than about 70% by weight of an anionic surfactant. The compositions of the present disclosure may comprise from about 10% to about 50%, or about 20% to about 70%, or about 30% to about 75%, or about 30% to about 65%, or about 35% to about 65%, or about 40% to about 60%, of an anionic surfactant.

The anionic surfactants may exist in an acid form, and the acid form may be neutralized to form a surfactant salt. Typical agents for neutralization include metal counterion bases, such as hydroxides, e.g., NaOH or KOH. Further suitable agents for neutralizing anionic surfactants in their acid forms include ammonia, amines, or alkanolamines. Non-limiting examples of alkanolamines include monoethanolamine, diethanolamine, triethanolamine, and other linear or branched alkanolamines known in the art; suitable alkanolamines include 2-amino-1-propanol, 1-aminopropanol, monoisopropanolamine, or 1-amino-3-propanol. Amine neutralization may be done to a full or partial extent, e.g., part of the anionic surfactant mix may be neutralized with sodium or potassium and part of the anionic surfactant mix may be neutralized with amines or alkanolamines.

Non-limiting examples of suitable anionic surfactants include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. Suitable anionic surfactants may be derived from renewable resources, waste, petroleum, or mixtures thereof. Suitable anionic surfactants may be linear, partially branched, branched, or mixtures thereof Alkoxylated alkyl sulfate materials comprise ethoxylated alkyl sulfate surfactants, also known as alkyl ether sulfates or alkyl polyethoxylate sulfates. Examples of ethoxylated alkyl sulfates include water-soluble salts, particularly the alkali metal, ammonium and alkylolammonium salts, of organic sulfuric reaction products having in their molecular structure an alkyl group containing from about 8 to about 30 carbon atoms and a sulfonic acid and its salts. (Included in the term "alkyl" is the alkyl portion of acyl groups. In some examples, the alkyl group contains from about 15 carbon atoms to about 30 carbon atoms. In other examples, the alkyl ether sulfate surfactant may be a mixture of alkyl ether sulfates, said mixture having an average (arithmetic mean) carbon chain length within the range of about 12 to 30 carbon atoms, and in some examples an average carbon chain length of about 12 to 15 carbon atoms, and an average (arithmetic mean) degree of ethoxylation of from about 1 mol to 4 mols of ethylene oxide, and in some examples an average (arithmetic mean) degree of ethoxylation of 1.8 mols of ethylene oxide. In further examples, the alkyl ether sulfate surfactant may have a carbon chain length between about 10 carbon atoms to about 18 carbon atoms, and a degree of ethoxylation of from about 1 to about 6 mols of ethylene oxide. In yet further examples, the alkyl ether sulfate surfactant may contain a peaked ethoxylate distribution.

Non-alkoxylated alkyl sulfates may also be added to the disclosed detergent compositions and used as an anionic surfactant component. Examples of non-alkoxylated, e.g., non-ethoxylated, alkyl sulfate surfactants include those produced by the sulfation of higher $C_8$-$C_{20}$ fatty alcohols. In some examples, primary alkyl sulfate surfactants have the general formula: $ROSO_3^-M^+$, wherein R is typically a linear $C_8$-$C_{20}$ hydrocarbyl group, which may be straight chain or branched chain, and M is a water-solubilizing cation. In some examples, R is a $C_{10}$-$C_{18}$ alkyl, and M is an alkali metal. In other examples, R is a $C_{12}/C_{14}$ alkyl and M is sodium, such as those derived from natural alcohols.

Other useful anionic surfactants can include the alkali metal salts of alkyl benzene sulfonates, in which the alkyl group contains from about 9 to about 15 carbon atoms, in straight chain (linear) or branched chain configuration. In some examples, the alkyl group is linear. Such linear alkylbenzene sulfonates are known as "LAS." In other examples, the linear alkylbenzene sulfonate may have an average number of carbon atoms in the alkyl group of from about 11 to 14.

In a specific example, the linear straight chain alkyl benzene sulfonates may have an average number of carbon atoms in the alkyl group of about 11.8 carbon atoms, which may be abbreviated as $C_{11.8}$ LAS.

Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Another example of a suitable alkyl benzene sulfonate is a modified LAS (MLAS), which is a positional isomer that contains a branch, e.g., a methyl branch, where the aromatic ring is attached to the 2 or 3 position of the alkyl chain.

The anionic surfactant may include a 2-alkyl branched primary alkyl sulfates have 100% branching at the $C_2$ position ($C_1$ is the carbon atom covalently attached to the alkoxylated sulfate moiety). 2-alkyl branched alkyl sulfates and 2-alkyl branched alkyl alkoxy sulfates are generally derived from 2-alkyl branched alcohols (as hydrophobes). 2-alkyl branched alcohols, e.g., 2-alkyl-1-alkanols or 2-alkyl primary alcohols, which are derived from the oxo process, are commercially available from Sasol, e.g., LIAL®, ISALCHEM® (which is prepared from LIAL® alcohols by a fractionation process). $C_{14}/C_{15}$ branched primary alkyl sulfate are also commercially available, e.g., namely LIAL® 145 sulfate.

The anionic surfactant may include a mid-chain branched anionic surfactant, e.g., a mid-chain branched anionic detersive surfactant, such as, a mid-chain branched alkyl sulphate and/or a mid-chain branched alkyl benzene sulphonate.

Additional suitable anionic surfactants include methyl ester sulfonates, paraffin sulfonates, α-olefin sulfonates, and internal olefin sulfonates.

The compositions disclosed herein may comprise an anionic surfactant selected from the group consisting of linear or branched alkyl benzene sulfonates, linear or branched alkoxylated alkyl sulfates, linear or branched alkyl sulfates, methyl ester sulfonates, paraffin sulfonates, α-olefin sulfonates, internal olefin sulfonates, and mixtures thereof. The compositions disclosed herein may comprise an anionic surfactant selected from the group consisting of linear or branched alkyl benzene sulfonates, linear or branched alkoxylated alkyl sulfates, linear or branched alkyl sulfates, and mixtures thereof. The compositions disclosed herein may comprise a 2-alkyl branched primary alkyl sulfate.

Nonionic Surfactant

The compositions disclosed herein may comprise a nonionic surfactant. Suitable nonionic surfactants include alkoxylated fatty alcohols. The nonionic surfactant may be selected from ethoxylated alcohols and ethoxylated alkyl phenols of the formula $R(OC_2H_4)_n$—OH, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15.

Other non-limiting examples of nonionic surfactants useful herein include: $C_8$-$C_{18}$ alkyl ethoxylates, such as, NEODOL® nonionic surfactants from Shell; $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, BA; $C_{14}$-$C_{22}$ mid-chain branched alkyl alkoxylates, $BAE_x$, wherein x is from 1 to 30; alkylpolysaccharides; specifically alkylpolyglycosides; polyhydroxy fatty acid amides; and ether capped poly(oxyalkylated) alcohol surfactants.

Suitable nonionic detersive surfactants also include alkyl polyglucoside and alkyl alkoxylated alcohol. Suitable nonionic surfactants also include those sold under the tradename Lutensol® from BASF.

Cationic Surfactant

The compositions disclosed herein may comprise a cationic surfactant. Non-limiting examples of cationic surfactants include: the quaternary ammonium surfactants, which can have up to 26 carbon atoms include: alkoxylate quaternary ammonium (AQA) surfactants; dimethyl hydroxyethyl quaternary ammonium; dimethyl hydroxyethyl lauryl ammonium chloride; polyamine cationic surfactants; cationic ester surfactants; and amino surfactants, e.g., amido propyldimethyl amine (APA).

Suitable cationic detersive surfactants also include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

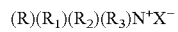

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, for example chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Zwitterionic Surfactant

The compositions disclosed herein may comprise a zwitterionic surfactant. Examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. Suitable examples of zwitterionic surfactants include betaines, including alkyl dimethyl betaine and cocodimethyl amidopropyl betaine, $C_8$ to $C_{18}$ (for example from $C_{12}$ to $C_{18}$) amine oxides, and sulfo and hydroxy betaines, such as N-alkyl-N,N-dimethylamino-1-propane sulfonate where the alkyl group can be $C_8$ to $C_{18}$.

Amphoteric Surfactant

The compositions disclosed herein may comprise an amphoteric surfactant. Examples of amphoteric surfactants include aliphatic derivatives of secondary or tertiary amines, or aliphatic derivatives of heterocyclic secondary and tertiary amines in which the aliphatic radical may be straight or branched-chain and where one of the aliphatic substituents contains at least about 8 carbon atoms, or from about 8 to about 18 carbon atoms, and at least one of the aliphatic substituents contains an anionic water-solubilizing group, e.g. carboxy, sulfonate, sulfate. Suitable amphoteric surfactants also include sarcosinates, glycinates, taurinates, and mixtures thereof.

Adjuncts

The compositions disclosed herein, particularly the dilute and compacted fluid detergents that are suitable for sale to consumers (final products), may comprise adjunct ingredients. The compositions disclosed herein may comprise an adjunct selected from the group consisting of a structurant, a builder, an organic polymeric compound, an enzyme, an enzyme stabilizer, a bleach system, a brightener, a hueing agent, a chelating agent, a suds suppressor, a conditioning agent, a humectant, a perfume, a perfume microcapsule, a filler or carrier, an alkalinity system, a pH control system, a buffer, an alkanolamine, and mixtures thereof.

Enzymes

The compositions described herein may comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a detergent composition, the aforementioned additional enzymes may be present at levels from about 0.00001% to about 2%, from about 0.0001% to about 1% or even from about 0.001% to about 0.5% enzyme protein by weight of the composition. The compositions disclosed herein may comprise from about 0.001% to about 1% by weight of an enzyme (as an adjunct), which may be selected from the group consisting of lipase, amylase, protease, mannanase, cellulase, pectinase, and mixtures thereof.

Enzyme Stabilizing System

The compositions may optionally comprise from about 0.001% to about 10%, or from about 0.005% to about 8%, or from about 0.01% to about 6%, by weight of the composition, of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, chlorine bleach scavengers and mixtures thereof, and are designed to address different stabilization problems depending on the type and physical form of the detergent composition. In the case of aqueous detergent compositions comprising protease, a reversible protease inhibitor, such as a boron compound, including borate, 4-formyl phenylboronic acid, phenylboronic acid and derivatives thereof, or compounds such as calcium formate, sodium formate and 1,2-propane diol may be added to further improve stability.

Builders

The compositions may comprise a builder. Built compositions typically comprise at least about 1% builder, based on the total weight of the composition. Liquid detergent compositions may comprise up to about 10% builder, and in some examples up to about 8% builder, of the total weight of the composition.

Suitable builders include aluminosilicates (e.g., zeolite builders, such as zeolite A, zeolite P, and zeolite MAP), silicates, phosphates, such as polyphosphates (e.g., sodium tri-polyphosphate), especially sodium salts thereof; carbonates, bicarbonates, sesquicarbonates, and carbonate minerals other than sodium carbonate or sesquicarbonate; organic mono-, di-, tri-, and tetracarboxylates, especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. Additional suitable builders may be selected from citric acid, lactic acid, fatty acid, polycarboxylate builders, for example, copolymers of acrylic acid, copolymers of acrylic acid and maleic acid, and copolymers of acrylic acid and/or maleic acid, and other suitable ethylenic monomers with various types of additional functionalities. Alternatively, the composition may be substantially free of builder.

Structurant/Thickeners

Suitable structurants/thickeners include di-benzylidene polyol acetal derivative. The fluid detergent composition may comprise from about 0.01% to about 1% by weight of a dibenzylidene polyol acetal derivative (DBPA), or from about 0.05% to about 0.8%, or from about 0.1% to about 0.6%, or even from about 0.3% to about 0.5%. The DBPA derivative may comprise a dibenzylidene sorbitol acetal derivative (DBS).

Suitable structurants/thickeners also include bacterial cellulose. The fluid detergent composition may comprise from about 0.005% to about 1% by weight of a bacterial cellulose network. The term "bacterial cellulose" encompasses any type of cellulose produced via fermentation of a bacteria of the genus *Acetobacter* such as CELLULON® by CPKelco U.S. and includes materials referred to popularly as microfibrillated cellulose, reticulated bacterial cellulose, and the like.

Suitable structurants/thickeners also include coated bacterial cellulose. The bacterial cellulose may be at least partially coated with a polymeric thickener. The at least partially coated bacterial cellulose may comprise from about 0.1% to about 5%, or even from about 0.5% to about 3%, by weight of bacterial cellulose; and from about 10% to about 90% by weight of the polymeric thickener. Suitable bacterial cellulose may include the bacterial cellulose described above and suitable polymeric thickeners include: carboxymethylcellulose, cationic hydroxymethylcellulose, and mixtures thereof.

Suitable structurants/thickeners also include cellulose fibers. The composition may comprise from about 0.01 to about 5% by weight of the composition of a cellulosic fiber. The cellulosic fiber may be extracted from vegetables, fruits or wood. Commercially available examples are Avicel® from FMC, Citri-Fi from Fiberstar or Betafib from Cosun.

Suitable structurants/thickeners also include non-polymeric crystalline hydroxyl-functional materials. The composition may comprise from about 0.01 to about 1% by weight of the composition of a non-polymeric crystalline, hydroxyl functional structurant. The non-polymeric crystalline, hydroxyl functional structurants generally may comprise a crystallizable glyceride which can be pre-emulsified to aid dispersion into the final fluid detergent composition. The crystallizable glycerides may include hydrogenated castor oil or "HCO" or derivatives thereof, provided that it is capable of crystallizing in the liquid detergent composition.

Suitable structurants/thickeners also include polymeric structuring agents. The compositions may comprise from about 0.01% to about 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof.

Suitable structurants/thickeners also include di-amido-gellants. The external structuring system may comprise a di-amido gellant having a molecular weight from about 150 g/mol to about 1,500 g/mol, or even from about 500 g/mol to about 900 g/mol. Such di-amido gellants may comprise at least two nitrogen atoms, wherein at least two of said nitrogen atoms form amido functional substitution groups. The amido groups may be different or the same. Non-limiting examples of di-amido gellants are: N,N'-(2S,2'S)-1,1'-(dodecane-1,12-diylbis(azanediyl))bis(3-methyl-1-oxobutane-2,1-diyl)diisonicotinamide; dibenzyl (2S,2'S)-1,1'-(propane-1,3-diylbis(azanediyl))bis(3-methyl-1-oxobutane-2,1-diyl)dicarbamate; dibenzyl (2S,2'S)-1,1'-(dodecane-1,12-diylbis(azanediyl))bis(1-oxo-3-phenylpropane-2,1-diyl)dicarbamate.

Polymeric Dispersing Agents

The cleaning composition may comprise one or more polymeric dispersing agents. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The cleaning composition may comprise one or more amphiphilic cleaning polymers such as the compound having the following general structure: bis(($C_2H_5O$)($C_2H_4O$)n) ($CH_3$)—$N^+$—$C_xH_{2x}$—$N^+$—($CH_3$)-bis(($C_2H_5O$)($C_2H_4O$)n), wherein n=from 20 to 30, and x=from 3 to 8, or sulphated or sulphonated variants thereof.

The cleaning composition may comprise amphiphilic alkoxylated grease cleaning polymers which have balanced hydrophilic and hydrophobic properties such that they remove grease particles from fabrics and surfaces. The amphiphilic alkoxylated grease cleaning polymers may comprise a core structure and a plurality of alkoxylate groups attached to that core structure. These may comprise alkoxylated polyalkylenimines, for example, having an inner polyethylene oxide block and an outer polypropylene oxide block. Such compounds may include, but are not limited to, ethoxylated polyethyleneimine, ethoxylated hexamethylene diamine, and sulfated versions thereof. Polypropoxylated derivatives may also be included. A wide variety of amines and polyalklyeneimines can be alkoxylated to various degrees. A useful example is 600 g/mol polyethyleneimine core ethoxylated to 20 EO groups per NH and is available from BASF. The detergent compositions described herein may comprise from about 0.1% to about 10%, and in some examples, from about 0.1% to about 8%, and in other examples, from about 0.1% to about 6%, by weight of the detergent composition, of alkoxylated polyamines.

Carboxylate Polymer—The detergent composition may also include one or more carboxylate polymers, which may optionally be sulfonated. Suitable carboxylate polymers include a maleate/acrylate random copolymer or a poly(meth)acrylate homopolymer. In one aspect, the carboxylate polymer is a poly(meth)acrylate homopolymer having a molecular weight from 4,000 Da to 9,000 Da, or from 6,000 Da to 9,000 Da.

Alkoxylated polycarboxylates may also be used in the detergent compositions herein to provide grease removal. Such materials are described in WO 91/08281 and PCT 90/01815. Chemically, these materials comprise poly(meth)acrylates having one ethoxy side-chain per every 7-8 (meth)acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but may be in the range of about 2000 to about 50,000. The detergent compositions described herein may comprise from about 0.1% to about 10%, and in some examples, from about 0.25% to about 5%, and in other examples, from about 0.3% to about 2%, by weight of the detergent composition, of alkoxylated polycarboxylates.

The compositions may include an amphiphilic graft co-polymer. A suitable amphiphilic graft co-polymer comprises (i) a polyethyelene glycol backbone; and (ii) and at least one pendant moiety selected from polyvinyl acetate, polyvinyl alcohol and mixtures thereof. A suitable amphilic graft co-polymer is Sokalan® HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is typically about 6000 and the weight ratio of the polyethylene oxide to polyvinyl acetate is about 40 to 60 and no more than 1 grafting point per 50 ethylene oxide units.

Soil Release Polymer

The detergent compositions of the present invention may also include one or more soil release polymers having a structure as defined by one of the following structures (I), (II) or (III):

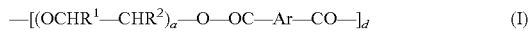

$$—[(OCHR^1—CHR^2)_a—O—OC—Ar—CO—]_d \quad (I)$$

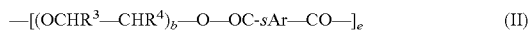

$$—[(OCHR^3—CHR^4)_b—O—OC\text{-}sAr—CO—]_e \quad (II)$$

$$—[(OCHR^5—CHR^6)_c—OR^7]_f \quad (III)$$

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.ellulosic polymer The cleaning compositions of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

Amines

Amines may be used in the compositions described herein for added removal of grease and particulates from soiled materials. The compositions described herein may comprise from about 0.1% to about 10%, in some examples, from about 0.1% to about 4%, and in other examples, from about 0.1% to about 2%, by weight of the detergent composition, of additional amines Non-limiting examples of additional amines may include, but are not limited to, polyetheramines, polyamines, oligoamines, triamines, diamines, pentamines, tetraamines, or combinations thereof. Specific examples of suitable additional amines include tetraethylenepentamine, triethylenetetraamine, diethylenetriamine, or a mixture thereof.

Bleaching Agents

The detergent compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the detergent compositions of the present invention may comprise from about 0.1% to about 50% or even from about 0.1% to about 25% bleaching agent by weight of the detergent composition.

Bleach Catalysts

The detergent compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Brighteners

Optical brighteners or other brightening or whitening agents may be incorporated at levels of from about 0.01% to about 1.2%, by weight of the composition, into the detergent compositions described herein. Commercial fluorescent brighteners suitable for the present invention can be classified into subgroups, including but not limited to: derivatives of stilbene, pyrazoline, coumarin, benzoxazoles, carboxylic acid, methinecyanines, dibenzothiophene-5,5-dioxide, azoles, 5- and 6-membered-ring heterocycles, and other miscellaneous agents.

In some examples, the fluorescent brightener is selected from the group consisting of disodium 4,4'-bis{[4-anilino-6-morpholino-s-triazin-2-yl]-amino}-2,2'-stilbenedisulfonate (brightener 15, commercially available under the tradename Tinopal AMS-GX by Ciba Geigy Corporation), disodium4,4'-bis{[4-anilino-6-(N-2-bis-hydroxyethyl)-s-triazine-2-yl]-amino}-2,2'-stilbenedisulonate (commercially available under the tradename Tinopal UNPA-GX by Ciba-Geigy Corporation), disodium 4,4'-bis{[4-anilino-6-(N-2-hydroxyethyl-N-methylamino)-s-triazine-2-yl]-amino}-2,2'-stilbenedisulfonate (commercially available under the tradename Tinopal SBM-GX by Ciba-Geigy Corporation). More preferably, the fluorescent brightener is disodium 4,4'-bis{[4-anilino-6-morpholino-s-triazin-2-yl]-amino}-2,2'-stilbenedisulfonate.

The brighteners may be added in particulate form or as a premix with a suitable solvent, for example nonionic surfactant, propanediol.

Fabric Hueing Agents

The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes also include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes for example that are classified as Blue, Violet, Red, Green or Black, and provide the desired shade either alone or in combination. Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Suitable polymeric dyes also include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. Suitable polymeric dyes also include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

The aforementioned fabric hueing agents can be used in combination (any mixture of fabric hueing agents can be used).

Encapsulates

The compositions may comprise an encapsulate. The encapsulate may comprise a core, a shell having an inner and outer surface, where the shell encapsulates the core.

The encapsulate may comprise a core and a shell, where the core comprises a material selected from perfumes; brighteners; dyes; insect repellants; silicones; waxes; flavors; vitamins; fabric softening agents; skin care agents, e.g., paraffins; enzymes; anti-bacterial agents; bleaches; sensates; or mixtures thereof; and where the shell comprises a material selected from polyethylenes; polyamides; polyvinylalcohols, optionally containing other co-monomers; polystyrenes; polyisoprenes; polycarbonates; polyesters; polyacrylates; polyolefins; polysaccharides, e.g., alginate and/or chitosan; gelatin; shellac; epoxy resins; vinyl polymers; water insoluble inorganics; silicone; aminoplasts, or mixtures thereof. When the shell comprises an aminoplast, the aminoplast may comprise polyurea, polyurethane, and/or polyureaurethane. The polyurea may comprise polyoxymethyleneurea and/or melamine formaldehyde.

The encapsulate may comprise a core, and the core may comprise a perfume. The encapsulate may comprise a shell, and the shell may comprise melamine formaldehyde and/or cross linked melamine formaldehyde. The encapsulate may comprise a core comprising a perfume and a shell comprising melamine formaldehyde and/or cross linked melamine formaldehyde Suitable encapsulates may comprise a core material and a shell, where the shell at least partially surrounds the core material. The core of the encapsulate comprises a material selected from a perfume raw material and/or optionally another material, e.g., vegetable oil, esters of vegetable oils, esters, straight or branched chain hydrocarbons, partially hydrogenated terphenyls, dialkyl phthalates, alkyl biphenyls, alkylated naphthalene, petroleum spirits, aromatic solvents, silicone oils, or mixtures thereof.

The wall of the encapsulate may comprise a suitable resin, such as the reaction product of an aldehyde and an amine. Suitable aldehydes include formaldehyde. Suitable amines include melamine, urea, benzoguanamine, glycoluril, or mixtures thereof. Suitable melamines include methylol melamine, methylated methylol melamine, imino melamine and mixtures thereof. Suitable ureas include, dimethylol urea, methylated dimethylol urea, urea-resorcinol, or mixtures thereof.

Suitable formaldehyde scavengers may be employed with the encapsulates, for example, in a capsule slurry and/or added to a composition before, during, or after the encapsulates are added to such composition.

Suitable capsules can be purchased from Appleton Papers Inc. of Appleton, Wis. USA.

Perfumes

Perfumes and perfumery ingredients may be used in the detergent compositions described herein. Non-limiting examples of perfume and perfumery ingredients include, but are not limited to, aldehydes, ketones, esters, and the like. Other examples include various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes may be included at a concentration ranging from about 0.01% to about 2% by weight of the detergent composition.

Dye Transfer Inhibiting Agents

Fabric detergent compositions may also include one or more materials effective for inhibiting the transfer of dyes from one fabric to another during the cleaning process. Generally, such dye transfer inhibiting agents may include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents may be used at a concentration of about 0.0001% to about 10%, by weight of the composition, in some examples, from about 0.01% to about 5%, by weight of the composition, and in other examples, from about 0.05% to about 2% by weight of the composition.

Chelating Agents

The detergent compositions described herein may also contain one or more metal ion chelating agents. Suitable molecules include copper, iron and/or manganese chelating agents and mixtures thereof. Such chelating agents can be selected from the group consisting of phosphonates, amino carboxylates, amino phosphonates, succinates, polyfunctionally-substituted aromatic chelating agents, 2-pyridinol-N-oxide compounds, hydroxamic acids, carboxymethyl inulins and mixtures thereof. Chelating agents can be present in the acid or salt form including alkali metal, ammonium, and substituted ammonium salts thereof, and mixtures thereof. Other suitable chelating agents for use herein are the commercial DEQUEST series, and chelants from Monsanto, Akzo-Nobel, DuPont, Dow, the Trilon® series from BASF and Nalco.

The chelant may be present in the detergent compositions disclosed herein at from about 0.005% to about 15% by weight, about 0.01% to about 5% by weight, about 0.1% to about 3.0% by weight, or from about 0.2% to about 0.7% by weight, or from about 0.3% to about 0.6% by weight of the detergent compositions disclosed herein.

Suds Suppressors

Compounds for reducing or suppressing the formation of suds can be incorporated into the detergent compositions described herein. Suds suppression can be of particular importance in the so-called "high concentration cleaning process" and in front-loading style washing machines. The detergent compositions herein may comprise from 0.1% to about 10%, by weight of the composition, of suds suppressor.

Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols.

Additional suitable antifoams are those derived from phenylpropylmethyl substituted polysiloxanes.

The detergent composition may comprise a suds suppressor selected from organomodified silicone polymers with aryl or alkylaryl substituents combined with silicone resin and a primary filler, which is modified silica. The detergent compositions may comprise from about 0.001% to about 4.0%, by weight of the composition, of such a suds suppressor.

The detergent composition comprises a suds suppressor selected from: a) mixtures of from about 80 to about 92% ethylmethyl, methyl(2-phenylpropyl) siloxane; from about 5 to about 14% MQ resin in octyl stearate; and from about 3 to about 7% modified silica; b) mixtures of from about 78 to about 92% ethylmethyl, methyl(2-phenylpropyl) siloxane; from about 3 to about 10% MQ resin in octyl stearate; from about 4 to about 12% modified silica; or c) mixtures thereof, where the percentages are by weight of the anti-foam.

Suds Boosters

If high sudsing is desired, suds boosters such as the $C_{10}$-$C_{16}$ alkanolamides may be incorporated into the detergent compositions at a concentration ranging from about 1% to about 10% by weight of the detergent composition. Some examples include the $C_{10}$-$C_{14}$ monoethanol and diethanol amides. If desired, water-soluble magnesium and/or calcium salts such as $MgCl_2$, $MgSO_4$, $CaCl_2$, $CaSO_4$, and the like, may be added at levels of about 0.1% to about 2% by weight of the detergent composition, to provide additional suds and to enhance grease removal performance.

Conditioning Agents

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. The high melting point fatty compound is included in the composition at a level of from about 0.1% to about 40%, preferably from about 1% to about 30%, more preferably from about 1.5% to about 16% by weight of the composition, from about 1.5% to about 8%.

The composition of the present invention may include a nonionic polymer as a conditioning agent.

Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. The concentration of the silicone conditioning agent typically ranges from about 0.01% to about 10%.

The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters.

Fabric Enhancement Polymers

Suitable fabric enhancement polymers are typically cationically charged and/or have a high molecular weight. Suitable concentrations of this component are in the range from 0.01% to 50%, preferably from 0.1% to 15%, more preferably from 0.2% to 5.0%, and most preferably from 0.5% to 3.0% by weight of the composition. The fabric enhancement polymers may be a homopolymer or be formed from two or more types of monomers. The monomer weight of the polymer will generally be between 5,000 and 10,000,000, typically at least 10,000 and preferably in the range 100,000 to 2,000,000. Preferred fabric enhancement polymers will have cationic charge densities of at least 0.2 meq/gm, preferably at least 0.25 meq/gm, more preferably at least 0.3 meq/gm, but also preferably less than 5 meq/gm, more preferably less than 3 meq/gm, and most preferably less than 2 meq/gm at the pH of intended use of the composition, which pH will generally range from pH 3 to pH 9, preferably between pH 4 and pH 8. The fabric enhancement polymers may be of natural or synthetic origin.

Pearlescent Agent

The laundry detergent compositions of the invention may comprise a pearlescent agent. Non-limiting examples of pearlescent agents include: mica; titanium dioxide coated mica; bismuth oxychloride; fish scales; mono and diesters of alkylene glycol. The pearlescent agent may be ethyleneglycoldistearate (EGDS).

Hygiene and Malodour

The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release $Ag^+$ or nano-silver dispersions.

Buffer System

The detergent compositions described herein may be formulated such that, during use in aqueous cleaning operations, the wash water will have a pH of between about 7.0 and about 12, and in some examples, between about 7.0 and about 11. Techniques for controlling pH at recommended usage levels include the use of buffers, alkalis, or acids, and are well known to those skilled in the art. These include, but are not limited to, the use of sodium carbonate, citric acid or sodium citrate, lactic acid or lactate, monoethanol amine or other amines, boric acid or borates, and other pH-adjusting compounds well known in the art.

The detergent compositions herein may comprise dynamic in-wash pH profiles. Such detergent compositions may use wax-covered citric acid particles in conjunction with other pH control agents such that (i) about 3 minutes after contact with water, the pH of the wash liquor is greater than 10; (ii) about 10 minutes after contact with water, the pH of the wash liquor is less than 9.5; (iii) about 20 minutes after contact with water, the pH of the wash liquor is less than 9.0; and (iv) optionally, wherein, the equilibrium pH of the wash liquor is in the range of from about 7.0 to about 8.5.

Water-Soluble Film

The compositions of the present disclosure may be encapsulated within a water-soluble film, for example, a film comprising polyvinyl alcohol (PVOH).

Other Adjunct Ingredients

A wide variety of other ingredients may be used in the detergent compositions herein, including other active ingredients, carriers, hydrotropes, processing aids, dyes or pigments, solvents for liquid formulations, and solid or other liquid fillers, erythrosine, colliodal silica, waxes, probiotics, surfactin, aminocellulosic polymers, Zinc Ricinoleate, perfume microcapsules, rhamnolipids, sophorolipids, glycopeptides, methyl ester sulfonates, methyl ester ethoxylates, sulfonated estolides, cleavable surfactants, biopolymers, silicones, modified silicones, aminosilicones, deposition aids, locust bean gum, cationic hydroxyethylcellulose polymers, cationic guars, hydrotropes (especially cumenesulfonate salts, toluenesulfonate salts, xylenesulfonate salts, and naphalene salts), antioxidants, BHT, PVA particle-encapsulated dyes or perfumes, pearlescent agents, effervescent agents, color change systems, silicone polyurethanes, opacifiers, tablet disintegrants, biomass fillers, fast-dry silicones, glycol distearate, hydroxyethylcellulose polymers, hydrophobically modified cellulose polymers or hydroxyethylcellulose polymers, starch perfume encapsulates, emulsified oils, bisphenol antioxidants, microfibrous cellulose structurants, properfumes, styrene/acrylate polymers, triazines, soaps, superoxide dismutase, benzophenone protease inhibitors, functionalized TiO2, dibutyl phosphate, silica perfume capsules, and other adjunct ingredients, silicate salts (e.g., sodium silicate, potassium silicate), choline oxidase, pectate lyase, mica, titanium dioxide coated mica, bismuth oxychloride, and other actives.

The compositions described herein may also contain vitamins and amino acids such as: water soluble vitamins and their derivatives, water soluble amino acids and their salts and/or derivatives, water insoluble amino acids viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, niacinamide, caffeine, and minoxidil.

The compositions of the present invention may also contain pigment materials such as nitroso, monoazo, disazo, carotenoid, triphenyl methane, triaryl methane, xanthene, quinoline, oxazine, azine, anthraquinone, indigoid, thionindigoid, quinacridone, phthalocianine, botanical, and natural colors, including water soluble components such as those having C.I. Names. The detergent compositions of the present invention may also contain antimicrobial agents.

Water

The compositions disclosed herein may comprise from about 1% to about 80%, by weight of the composition, water. When the composition is a heavy duty liquid detergent composition, the composition typically comprises from about 40% to about 80% water. When the composition is a compact liquid detergent, the composition typically comprises from about 20% to about 60%, or from about 30% to about 50% water. When the composition is in unit dose form, for example, encapsulated in water-soluble film, the composition typically comprises less than 20%, or less than 15%, or less than 12%, or less than 10%, or less than 8%, or less than 5% water. The composition may comprise from about 1% to 20%, or from about 3% to about 15%, or from about 5% to about 12%, by weight of the composition, water. When the composition is in unitized dose form, for example, encapsulated in water-soluble film, the composition typically comprises less than 20%, or less than 15%, or less than 12%, or less than 10%, or less than 8%, or less than 5% water. The composition may comprise from about 1% to 20%, or from about 3% to about 15%, or from about 5% to about 12%, by weight of the composition, water.

Methods of Use

The present invention includes methods for cleaning soiled material. As will be appreciated by one skilled in the art, the cleaning compositions of the present invention are suited for use in laundry pretreatment applications, laundry cleaning applications, and home care applications.

Such methods include, but are not limited to, the steps of contacting cleaning compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the cleaning compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry cleaning composition in accord with the invention. An "effective amount" of the cleaning composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 20:1. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The cleaning compositions herein may be used for laundering of fabrics at reduced wash temperatures. These methods of laundering fabric comprise the steps of delivering a laundry cleaning composition to water to form a wash liquor and adding a laundering fabric to said wash liquor, wherein the wash liquor has a temperature of from about 0° C. to about 20° C., or from about 0° C. to about 15° C., or from about 0° C. to about 9° C. The fabric may be contacted to the water prior to, or after, or simultaneous with, contacting the laundry cleaning composition with water.

Another method includes contacting a nonwoven substrate impregnated with an embodiment of the cleaning composition with soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SONTARA® by DuPont and POLYWEB® by James River Corp.

Hand washing/soak methods, and combined handwashing with semi-automatic washing machines, are also included.

Hard Surface Cleaning Methods, Including Dishwashing Methods

Methods for cleaning hard surfaces, including machine-dishwashing or hand dishwashing soiled dishes, tableware, silverware, or other kitchenware, are included. Hard surfaces may include household hard surfaces, including any kind of surface typically found in and around houses like kitchens, bathrooms, e.g., floors, walls, tiles, windows, cupboards, sinks, showers, shower plastified curtains, wash basins, WCs, fixtures and fittings and the like made of different materials like ceramic, vinyl, no-wax vinyl, linoleum, melamine, glass, Inox®, Formica®, any plastics, plastified wood, metal or any painted or varnished or sealed surface and the like. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments.

A method for machine dishwashing comprises treating soiled dishes, tableware, silverware, or other kitchenware with an aqueous liquid having dissolved or dispensed therein an effective amount of a machine dishwashing composition in accord with the invention. By an effective amount of the machine dishwashing composition it is meant from about 8 g to about 60 g of product dissolved or dispersed in a wash solution of volume from about 3 L to about 10 L.

One method for hand dishwashing comprises dissolution of the cleaning composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the cleaning composition onto soiled dishes, tableware, silverware, or other kitchenware, then hand scrubbing, wiping, or rinsing the soiled dishes, tableware, silverware, or other kitchenware. In some examples, an effective amount of cleaning composition for hand dishwashing is from about 0.5 ml. to about 20 ml. diluted in water.

Packaging for the Compositions

The cleaning compositions described herein can be packaged in any suitable container including those constructed from paper, cardboard, plastic materials, and any suitable laminates. A suitable packaging type is described in European Application No. 94921505.7.

Single- or Multi-Compartment Pouch Additive

The cleaning compositions described herein may also be packaged as a single- or multi-compartment cleaning composition.

COMBINATIONS

Specifically contemplated combinations of the disclosure are herein described in the following lettered paragraphs. These combinations are intended to be illustrative in nature and are not intended to be limiting.

A. A cleaning composition comprising: from about 1% to about 70%, by weight of the composition, of a surfactant system, and from about 0.1% to about 10% of an esteramine according to Formula (I) and/or a salt thereof,

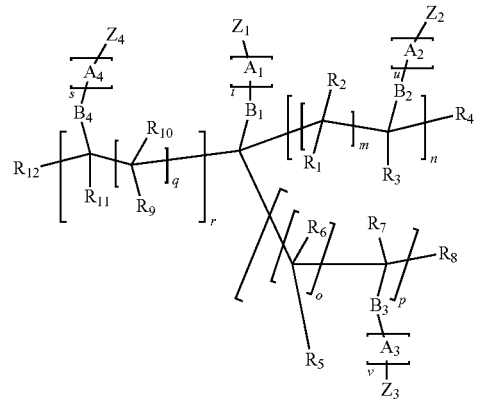

(Formula I)

wherein independently from each other n being an integer from 0 to 12, m being an integer for each repetition unit n independently selected from 0 to 12; p being an integer from 0 to 12, o being an integer for each repetition unit p independently selected from 0 to 12; r being an integer from 0 to 12, q being an integer for each repetition unit r independently selected from 0 to 12; s being an integer from 0 to 100; t being an integer from 1 to 100; u being an integer from 0 to 100; v being an integer from 0 to 100; with the sum of s, t, u, and v being equal to or greater than 1; $A_1$, $A_2$, $A_3$, and $A_4$ are independently from each other and independently for each repetition unit s, t, u, or v, selected from the list consisting of ethyleneoxy group, isopropyleneoxy group, propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein when s, t, u, and/or v equal to or greater than 1, the oxygen atom of the first $A_1$, $A_2$, $A_3$, and $A_4$ group is bound to the B group and the subsequent $A_1$, $A_2$, $A_3$, and $A_4$ groups, when they exist, are bound via an oxygen atom to the previous $A_1$, $A_2$, $A_3$, and $A_4$ group; $B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups; $R_4$, $R_8$, and $R_{12}$ being selected from the group consisting of H, linear alkyl, branched alkyl, and cycloalkyl; $R_1$, $R_2$, and $R_3$ being independently for each repetition unit o of each repetition unit p being selected from the group consisting of H, linear alkyl, branched alkyl, and cycloalkyl; $R_5$, $R_6$, and $R_7$ being independently for each repetition unit m of each repetition unit n being selected from the group consisting of H, linear alkyl, branched alkyl, and cycloalkyl; $R_9$, $R_{10}$, and $R_{11}$ being independently for each repetition unit q of each repetition unit r being selected from the group consisting of H, linear alkyl, branched alkyl, and cycloalkyl; $Z_1$, $Z_2$, $Z_3$, and/or $Z_4$, if present, being independently selected from the group consisting of —OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *,

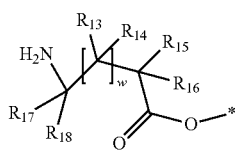

(Formula II)

with independently from each other w being an integer from 0 to 12, $R_{13}$ and $R_{14}$ independently for each repetition unit w being selected from the group consisting of H, linear alkyl, branched alkyl, and cycloalkyl; $R_{15}$, $R_{16}$, $R_{17}$, and $R_{18}$ being selected from the group consisting of H, linear alkyl, branched alkyl, and cycloalkyl; with the proviso that at least one of $Z_1$, $Z_2$, $Z_3$, and/or $Z_4$ is present and is not —OH.

B. A cleaning composition according to paragraph A, wherein n, p, and r are each equal to zero, and $Z_1$ is selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the proviso of at least one group $R_4$, $R_8$, and/or $R_{12}$ containing at least 7 or more carbon atoms;

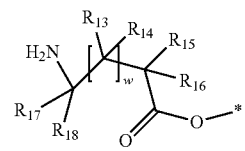

(Formula II)

with independently from each other w being an integer from 0 to 12, $R_{13}$ and $R_{14}$ independently for each repetition unit w being selected from the group consisting of H, linear alkyl, branched alkyl, and cycloalkyl; $R_{15}$, $R_{16}$, $R_{17}$, and $R_{18}$ being selected from the group consisting of H, linear alkyl, branched alkyl, and cycloalkyl.

C. A cleaning composition according to any of paragraphs A-B, wherein p and r are both equal to 0, n is at least 1, and $Z_1$ and $Z_2$, are independently selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II),

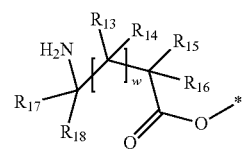

(Formula II)

with independently from each other w being an integer from 0 to 12, $R_{13}$ and $R_{14}$ independently for each repetition unit w being selected from the group consisting of H, linear alkyl, branched alkyl, and cycloalkyl; $R_{15}$, $R_{16}$, $R_{17}$, and $R_{18}$ being selected from the group consisting of H, linear alkyl, branched alkyl, and cycloalkyl, wherein said compound according to Formula (II) connects to the compound according to Formula (I) via the bond labeled with *, with the proviso that at least one substituent $Z_1$ and/or $Z_2$ is not OH, and with the proviso that $R_3$ contains equal to or more than 2 carbon atoms.

D. A cleaning composition according to any of paragraphs A-C, wherein n and p are individually equal to or greater than 1, r is equal to or greater than 0, and $Z_1$, and/or $Z_2$, and/or $Z_3$, and/or $Z_4$, independently for each repetition unit n, p, and r, are selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II),

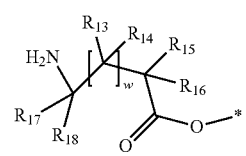

(Formula II)

with independently from each other w being an integer from 0 to 12, $R_{13}$ and $R_{14}$ independently for each repetition unit w being selected from the group consisting of H, linear alkyl, branched alkyl, and cycloalkyl; $R_{15}$, $R_{16}$, $R_{17}$, and $R_{18}$ being selected from the group consisting of H, linear alkyl, branched alkyl, and cycloalkyl, wherein said compound according to Formula (II) connects to the compound according to Formula (I) via the bond labeled with *, with the proviso that at least one substituent $Z_1$, and/or $Z_2$, and/or $Z_3$, and/or $Z_1$, is not OH, and wherein if n and p equal to 1 and r equal to 0 at least one unit $A_1$, $A_2$, or $A_3$ is selected from the group consisting of propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group.

E. A cleaning composition according to any of paragraphs A-D, wherein the composition comprises a salt of the esteramine according to claim 1, wherein the salt is formed by at least partial protonation of the amine group by an acid being a protic organic or inorganic acid.

F. A cleaning composition according to any of paragraphs A-E, wherein the composition comprises a salt of the esteramine according to any of paragraphs A-E, wherein the salt is formed by at least partial protonation of the amine group by an acid being selected from the group consisting of methanesulfonic acid, hydrochloric acid, hydrobromic acid, sulfuric acid, phosphoric acid, toluene sulfonic acid, citric acid, lactic acid, $C_{12}$-$C_{18}$ fatty acid, alkyl benzene sulfonic acids, alkyl sulphonic acids, alkyl sulfate acids, alkyl ethyoxysulfate acids, alkoxylated or non-alkoxylated copolymers of acrylic acid and maleic acid, and mixtures thereof.

G. A cleaning composition according to any of paragraphs A-F, wherein $A_1$, $A_2$, $A_3$, and $A_4$ are, independently from each other and independently for each repetition unit s, t, u, and/or v, selected from the list consisting of ethyleneoxy group, propyleneoxy group, and 1,2-butyleneoxy group.

H. A cleaning composition according to any of paragraphs A-G, wherein p, r, and n are all equal to 0, $Z_1$ is selected from the group consisting of alanine, glycine, lysine, and a compound according to Formula (II), wherein w is an integer in the range of from 1 to 4, and wherein the compound according to Formula (II) connects to the compound according to Formula (I) via the bond labeled with *, with the proviso of at least one group $R_4$, $R_8$, and/or $R_{12}$ containing at least 7 or more carbon atoms;

I. A cleaning composition according to any of paragraphs A-H, wherein p and r are both equal to 0, and n being at least 1, $Z_1$ and $Z_2$, are independently selected from the group consisting of OH, alanine, glycine, lysine, and a compound according to Formula (II), wherein w is an integer in the range of from 1 to 4, wherein the compound according to Formula (II) connects to the compound according to Formula (I) via the bond labeled with *, with the proviso that at least one substituent $Z_1$ and/or $Z_2$ is not OH, and with the proviso that $R_3$ contains equal to or more than 2 carbon atoms.

J. A cleaning composition according to any of paragraphs A-I, wherein p and r are both equal to 0, and n being at least 1, wherein m is equal to 1 and $R_1$ and $R_2$ are both linear $C_2$ to $C_4$ alkyl groups.

K. A cleaning composition according to any of paragraphs A-J, wherein when n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of OH, alanine, glycine, lysine, and a compound according to Formula (II), wherein w is an integer in the range of from 1 to 4, wherein the compound according to Formula (II) connects to the compound according to Formula (I) via the bond labeled with *, with the provisio that at least one substituent $Z_1$, and/or $Z_2$, and/or $Z_3$, and/or $Z_4$, is not OH.

L. A cleaning composition according to any of paragraphs A-K, wherein n and p are both equal to 1, r is equal to 0, m and o are both equal to 0, B1 is equal to a chemical bond, $R_3$, $R_4$, $R_7$, $R_8$, and $R_{12}$ are all equal to H.

M. A cleaning composition according to any of paragraphs A-L, wherein n and p are both equal to 1, r is equal to 0, m and o are both equal to 0, B1 is equal to a methylene, $R_3$, $R_4$, $R_7$, and $R_8$ are all equal to H, and $R_{12}$ is equal to ethyl.

N. A cleaning composition according to any of paragraphs A-M, wherein the surfactant system comprises one or more surfactants selected from anionic surfactants, cationic surfactants, non-ionic surfactants, amphoteric surfactants, and mixtures thereof.

O. A cleaning composition according to any of paragraphs A-N, wherein the cleaning composition further comprises an adjunct cleaning additive selected from the group consisting of builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, perfumes, and mixtures thereof.

P. A cleaning composition according to any of paragraphs A-O, wherein the adjunct cleaning additive comprises enzymes, preferably enzymes selected from protease, amylase, and lipase, more preferably lipase.

Q. A cleaning composition comprising: from about 1% to about 70%, by weight of the composition, of a surfactant system, and from about 0.1% to about 10% of an esteramine, and/or salt thereof, obtainable by: (a) reacting an alcohol according to Formula (III)

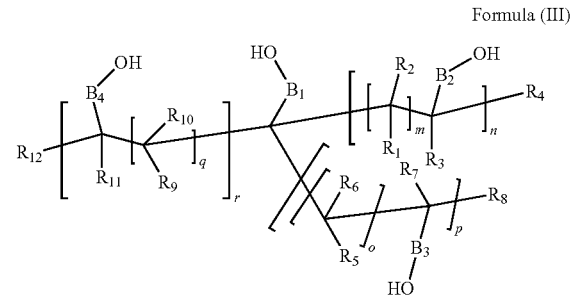

Formula (III)

wherein independently from each other: n being an integer from 0 to 12, m being an integer for each repetition unit n independently selected from 0 to 12; p being an integer from 0 to 12, o being an integer for each repetition unit p independently selected from 0 to 12; r being an integer from 0 to 12, q being an integer for each repetition unit r independently selected from 0 to 12; $B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups; $R_4$, $R_8$, and $R_{12}$ being selected from the group consisting of H, linear alkyl, branched alkyl, and cycloalkyl; $R_1$, $R_2$, and $R_3$ being independently for each repetition unit o of each repetition unit p being selected from the group consisting of H, linear alkyl, branched alkyl, and cycloalkyl; $R_5$, $R_6$, and $R_7$ being independently for each repetition unit m of each repetition unit n being selected from the group consisting of H, linear alkyl, branched alkyl, and cycloalkyl; $R_9$, $R_{10}$, and $R_{11}$ being independently for each repetition unit q of each repetition unit r being selected from the group consisting of H, linear alkyl, branched alkyl, and cycloalkyl; with one or more $C_2$ to $C_{16}$ alkylene oxide; followed by (b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof;

(Formula IV)

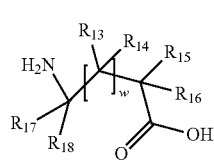

with w being an integer from 0 to 12, $R_{13}$ and $R_{10}$ independently for each repetition unit w being selected from the group consisting of H, linear alkyl, branched alkyl, and cycloalkyl; $R_{15}$, $R_{16}$, $R_{17}$, and $R_{18}$ being selected from the group consisting of H, linear alkyl, branched alkyl, and cycloalkyl.

R. A cleaning composition according to paragraph Q, wherein the molar ratio of alcohol according to Formula (III) to total $C_2$ to $C_{12}$ alkylene oxide is in the range of from 1:1 to 1:400.

S. A cleaning composition according to any of paragraphs Q-R, wherein the molar ratio of the acid to the hydroxyl groups of the alkoxylated alcohol is in the range of from 0.1:1 to 1:1.

T. A method of pretreating or treating a soiled fabric, the method comprising the step of contacting the soiled fabric with the cleaning composition according to any of paragraphs A-S, preferably wherein the soiled fabric comprises a greasy stain.

U. A use of the esteramine and/or salt thereof according to any of paragraphs A-S in cleaning compositions, preferably laundry compositions, for removal of stains, preferably removal of greasy stains, more preferably the removal of greasy stains in wash water having a temperature of 30° C. or less.

TEST METHODS $^1$H NMR measured in MeOD with Bruker Avance 400 MHz spectrometer.

pH is measured in 10% aqueous solution.

Hydroxyl values are measured according to DIN 53240-1.

Molecular weight of polyalkylene oxides (e.g. polyethylene glycol) is calculated from the measured hydroxyl values by following formula:

Molecular weight [g/mol]=1000/(hydroxyl value [mgKOH/g]/56.11)×hydroxyl groups per molecule

EXAMPLES

The examples provided below are intended to be illustrative in nature and are not intended to be limiting.

Synthesis Examples

Synthesis Example 1: 2-Propylheptanol, Ethoxylated with 3 Mole Ethylene Oxide, Ester with 6-Amino Hexane Acid, Methane Sulfonic Acid Salt In a 4-neck vessel with thermometer, reflux condenser, nitrogen inlet, dropping funnel, and stirrer, 58.1 g 2-Propylheptanol, ethoxylated with 3 mole ethylene oxide and 26.2 g 6-amino hexane acid are placed and heated to 90° C. To the mixture 19.6 g methane sulfonic acid is added within 10 minutes. The reaction mixture is heated to 130° C. and is stirred for 0.5 hours at 130° C. Vacuum (2 mbar) is applied and the reaction mixture is stirred for additional 10 hours at 130° C. 90.5 g of a light brown solid is obtained. $^1$H-NMR in MeOD indicates complete conversion to 6-amino hexane acid acid—triethylene glycol 2-propyl-heptylether ester as methane sulfonic acid salt.

Synthesis Example 2: $C_{13}$-Oxoalcohol Ethoxylated with 3 Mole Ethylene Oxide, Ester with 6-Amino Hexane Acid, Methane Sulfonic Acid Salt In a 4-neck vessel with thermometer, reflux condenser, nitrogen inlet, dropping funnel, and stirrer, 65.93 g $C_{13}$ oxoalcohol ethoxylated with 3 mole ethylene oxide and 26.23 g 6-amino hexane acid are placed and heated to 90° C. To the mixture 19.6 g methane sulfonic acid is added within 10 minutes. The reaction mixture is heated to 135° C. and is stirred for 7.0 hours at 135° C. Vacuum (5 mbar) is applied and the reaction mixture is stirred for additional 3 hours at 130° C. 101.95 g of a light brown solid is obtained. $^1$H-NMR in MeOD indicates complete conversion to 6-amino hexane acid acid—triethylene glycol $C_{13}$-oxoalcohol ester as methane sulfonic acid salt.

Synthesis Example 3: Sorbitol, Propoxylated with 12 Mole Propylene Oxide, Ester with 2 Mole 6-Aminohexane Acid, Methane Sulfonic Acid Salt 3a Sorbitol, Propoxylated with 12 Mole Propylene Oxide:
In a 2l autoclave 278.85 g sorbitol and 2.65 g potassium tert-butylate are placed and the mixture is heated to 140° C. The vessel is purged three times with nitrogen and 1005.4 g propylene oxide is added in portions within 15 h. To complete the reaction, the mixture was allowed to post-react for additional 5 h at 140° C. The reaction mixture is stripped with nitrogen and volatile compounds are removed in vacuo at 80° C. After filtration 1325.0 g of a light yellowish oil is obtained (hydroxy value: 375 mgKOH/g).

3b Sorbitol, Propoxylated with 12 Mole Propylene Oxide, Ester with 2 Mole 6-Aminohexane Acid, Methane Sulfonic Acid Salt In a 4-neck vessel with thermometer, nitrogen inlet, dropping funnel, and stirrer 88.14 g sorbitol propoxylated with 12 mole propylene oxide and 26.0 g 6-amino hexane acid are placed. The mixture is heated to 50° C., and 19.6 g methane sulfonic acid is added within 10 minutes under a constant stream of nitrogen. The temperature is allowed to rise to 60° C. during the addition. The reaction mixture is heated to 135° C. and is stirred for 4 hours at 135° C.

Vacuum (5 mbar) is applied and the reaction mixture is stirred for additional 11.0 hours at 130° C. 121.0 g of a brown solid is obtained. $^1$H-NMR in MeOD indicates 33% conversion of hydroxyl groups into esterified hydroxyl groups.

Synthesis Example 4: Sorbitol, Alkoxylated with 18 Mole Ethylene Oxide and 6 Mole Propylene Oxide, Ester with 2 Mole 6-Aminohexane Acid, Methane Sulfonic Acid Salt 4a Sorbitol, Alkoxylated with 18 Mole Ethylene Oxide and 6 Mole Propylene Oxide In a 2 l autoclave 148.7 g sorbitol and 2.1 g potassium tert.-butylate are placed and the mixture is heated to 130° C. The vessel is purged three times with nitrogen and 634.3 g ethylene oxide is added within 20 h. The mixture is stirred for additional 5 h, followed by the addition of 278.8 g propylene oxide in portions within 10 h. To complete the reaction, the mixture is allowed to post-react for additional 5 h at 130° C. The reaction mixture was stripped with nitrogen and volatile compounds were removed in vacuo at 80° C. After filtration 1060.0 g of a light yellowish oil was obtained (hydroxy value: 250 mgKOH/g).

4b Sorbitol, Alkoxylated with 18 Mole Ethylene Oxide and 6 Mole Propylene Oxide, Ester with 6 Mole DL-Alanine, Methane Sulfonic Acid Salt In a 4-neck vessel with thermometer, nitrogen inlet, dropping funnel, and stirrer 105.8 g sorbitol, alkoxylated with 18 mole ethylene oxide and 6 mole propylene oxide and 42.8 g DL-alanine are placed. The mixture is heated to 50° C., and 47.1 g methane sulfonic acid is added within 10 minutes under a constant stream of nitrogen. The temperature is allowed to rise to 60° C. during the addition. The reaction mixture is heated to 135° C. and is stirred for 13 hours at 135° C. 186.0 g of a brown solid is obtained. $^1$H-NMR in MeOD indicates 100% conversion of hydroxyl groups into esterified hydroxyl groups.

Comparative Example 1: Butyltriglycol Ester with 6-Amino Hexane Acid, Methane Sulfonic Acid Salt In a 4-neck vessel with thermometer, reflux condenser, nitrogen inlet, dropping funnel, and stirrer, 64.39 g butyltriglycol and 39.35 g 6-amino hexane acid are placed and heated to 90° C. To the mixture 29.4 g methane sulfonic acid is added within 10 minutes. The reaction mixture is heated to 135° C. and is stirred for 4 hours at 135° C. Vacuum (5 mbar) is applied and the reaction mixture is stirred for additional 13.5 hours at 130° C. 122.0 g of a light brown solid is obtained. $^1$H-NMR in MeOD indicates complete conversion to 6-amino hexane acid acid—butyltriglycol ester as methane sulfonic acid salt.

Comparative Example 2: Polyethylene Glycol, $M_w$ Approx. 200 g/Mol; Ester with 6-Amino Hexane Acid, Methane Sulfonic Acid Salt In a 4-neck vessel with thermometer, reflux condenser, nitrogen inlet, dropping funnel, and stirrer, 30.0 g polyethylene glycol ($M_w$ approx. 200 g/mol) and 39.35 g 6-amino hexane acid are placed and heated to 90° C. To the mixture 29.4 g methane sulfonic acid is added within 10 minutes. The reaction mixture is heated to 135° C. and is stirred for 4 hours at 135° C. Vacuum (5 mbar) is applied and the reaction mixture is stirred for additional 22 hours at 135° C. 97.0 g of a light brown solid is obtained. $^1$H-NMR in MeOD indicates complete conversion to 6-amino hexane acid acid—polyethylene glycol ester as methane sulfonic acid salt.

Performance Examples

Performance Example 1: Use as Additives in Detergents

Technical stain swatches of blue knitted cotton containing Bacon Grease were purchased from Warwick Equest Ltd. The stains were washed for 30 min in a launder-o-meter (manufactured by SDL Atlas) at room temperature using per canister 500 mL of washing solution, 20 metal balls and ballast fabrics. The washing solution contained 5000 ppm of detergent composition DC1 (table 1). Water hardness was 2.5 mM ($Ca^{2+}$:$Mg^{2+}$ was 4:1). Additives were added to the washing solution of each canister separately and in the amount as detailed below. After addition, the pH value was re-adjusted to the pH value of washing solution without additive.

Standard colorimetric measurement was used to obtain L*, a* and b* values for each stain before and after the washing. From L*, a* and b* values the stain level were calculated as color difference ΔE (calculated according to DIN EN ISO 11664-4) between stain and untreated fabric. Stain removal from the swatches was calculated as follows:

$$\text{Stain Removal Index } (SRI) = \frac{\Delta E_{initial} - \Delta E_{washed}}{\Delta E_{initial}} \times 100$$

$\Delta E_{initial}$ = Stain level before washing $\Delta E_{washed}$ = Stain level after washing Stain level corresponds to the amount of grease on the fabric. The stain level of the fabric before the washing ($\Delta E_{initial}$) is high, in the washing process stains are removed and the stain level after washing is smaller ($\Delta E_{washed}$). The better the stains have been removed the lower the value for $\Delta E_{washed\_}$ will be and the higher the difference will be to $\Delta E_{initial}$. Therefore, the value of stain removal index increases with better washing performance Results are shown in Table 2.

TABLE 1

| Detergent composition DC1 | |
|---|---|
| Ingredients of liquid detergent composition DC1 | percentage by weight |
| n-$C_{10}$-$C_{13}$-alkylbenzene sulfonic acid | 5.3 |
| coconut $C_{12}$-$C_{18}$ fatty acid | 2.4 |
| sodium laureth sulfate + 2 EO | 7.7 |
| potassium hydroxide | 2.2 |
| C13-C15- oxo alcohol + 7 EO | 5.4 |
| 1,2 propylene glycol | 6 |
| Ethanol | 2 |
| water | To Balance |
| pH of detergent composition DC1 = 8.0 | |

TABLE 2

Washing Experiment

| | SRI, Bacon Grease Cleaning |
|---|---|
| Without additive | 26.1 |
| With Synthesis Example 1: $C_{10}$-Guerbetalcohol (2-Propylheptanol) with 3 mole ethylenoxide, ester with 6-amino hexane acid, methane sulfonic acid salt; 0.046 g per wash | 31.8 |
| With Synthesis Example 2: $C_{13}$ Oxoalcohol ethoxylated with 3 mole ethylene oxide, ester with 6-amino hexane acid, methane sulfonic acid salt; 0.045 g per wash | 31.9 |
| With Comparative Example 1: Butyltriglycol ester with 6-amino hexane acid, methane sulfonic acid salt; 0.049 g per wash | 28.0 |
| With Comparative Example 2: Polyethylenglycol, $M_w$ approx. 200 g/mol; ester with 6-amino hexane acid, methane sulfonic acid salt 0.057 g per wash | 28.1 |

As shown in Table 2 above, detergent compositions that included compounds according to Synthesis Examples 1 or 2 provided improved stain removal on bacon grease compared to detergent compounds that included compounds according to Comparative Examples 1 or 2.

Performance Example 2: Use as Additives in Detergents

Technical stain wfk20D (polyester/cotton 65/35, soil: pigment/sebum) from wfk Testgewebe GmbH, are used. The washing procedure and the stain analysis is substantially the same as described above, but with 1584 ppm of detergent composition DC2. The pH of the washing solution prior to washing with and without additives was adjusted in each case to pH 8.0. The detergent formulation DC2 is shown in Table 3, and test results are shown in Tables 4 and 5.

TABLE 3

Detergent composition DC2

| Ingredients of liquid detergent composition DC2 | percentage by weight |
|---|---|
| linear $C_{11.8}$-alkylbenzene sulfonic acid | 17.6 |
| C12-C15 alkyl ethoxy (1.8) sulfate | 4.4 |
| C12-C14 alcohol + 9 ethylene oxide | 0.9 |
| C12-C18 fatty acid | 1.1 |
| C12-C14 amine oxide | 0.8 |
| chelant | 2.8 |
| solvent | 14.8 |
| brightener | 0.2 |
| sodium hydroxide | 1.9 |
| water | To Balance |

TABLE 4

| Experiment 1 | SRI, wfk 20D |
|---|---|
| Without additive | 42.4 |
| Synthesis Example 4: Sorbitol propoxylated, ester with ester with 6-amino hexane acid, methane sulfonic acid salt; 0.024 g per wash | 47.1 |

TABLE 5

| Experiment 2 | SRI, wfk 20D |
|---|---|
| Without additive | 40.3 |
| Synthesis Example 5: Sorbitol ethoxylated and propoxylated, ester with alanine, methane sulfonic acid salt; 0.024 g per wash | 45.5 |

As shown above in Tables 4 and 5, compositions that include compounds according to Synthesis Examples 4 and 5 provide improved stain removal.

Formulation Examples

Formulation Example 1. Heavy-Duty Liquid Laundry Detergent Compositions (North America)

TABLE 6

| | 1 (wt %) | 2 (wt %) | 3 (wt %) |
|---|---|---|---|
| AES $C_{12-15}$ alkyl ethoxy (1.8) sulfate | 10.9 | 10.9 | 11.1 |
| Alkyl benzene sulfonate [2] | 1.56 | 1.56 | 9.86 |
| Sodium formate | 2.66 | 2.66 | 0.11 |
| Calcium formate | — | — | 0.097 |
| Sodium hydroxide | 0.21 | 0.21 | 0.68 |
| Monoethanolamine (MEA) | 1.65 | 1.65 | 2.80 |
| Diethylene glycol (DEG) | 4.10 | 4.10 | 1.23 |
| Propylene glycol | — | — | 8.39 |
| AE9[3] | 0.40 | 0.40 | — |
| C16AE7 | 3.15 | 3.15 | — |
| NI 24-9[13] | — | — | 0.97 |
| Esteramine[11] | 1.04 | 2.30 | 1.00 |
| Chelant[4] | 0.18 | 0.18 | 0.29 |
| Citric Acid | 1.70 | 1.70 | 2.83 |
| $C_{12-18}$ Fatty Acid | 1.47 | 1.47 | 1.09 |
| Borax | 1.19 | 1.19 | 2.00 |
| Ethanol | 1.44 | 1.44 | 1.47 |
| Ethoxylated Polyethyleneimine [1] | 1.35 | 1.35 | 1.85 |
| Amphiphilic alkoxylated grease cleaning polymer[12] | — | — | 0.940 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 0.40 | 0.40 | 1.40 |
| 1,2-Propanediol | 2.40 | 2.40 | — |
| Protease (54.5 mg active/g)[9] | 0.89 | 0.89 | 0.95 |
| Mannanase: Mannaway ® (25.6 mg active/g)[5] | 0.04 | 0.04 | — |

TABLE 6-continued

|  | 1 (wt %) | 2 (wt %) | 3 (wt %) |
|---|---|---|---|
| Xyloglucanase: Whitezyme ® (20 mg active/g)[14] | — | — | 0.04 |
| Cellulase: Carezyme ™ (11.63 mg active/g)[15] | — | — | 0.10 |
| Amylase: Natalase ® (29 mg active/g)[5] | 0.14 | 0.14 | 0.34 |
| Fluorescent Whitening Agents[10] | 0.10 | 0.10 | 0.15 |
| Water, perfume, dyes & other components |  | Balance |  |

[1] Polyethyleneimine (MW = 600) with 20 ethoxylate groups per —NH.
[2] Linear alkylbenzenesulfonate having an average aliphatic carbon chain length $C_{11}$-$C_{12}$ supplied by Stepan, Northfield, Illinois, USA
[3] AE9 is $C_{12-13}$ alcohol ethoxylate, with an average degree of ethoxylation of 9, supplied by Huntsman, Salt Lake City, Utah, USA.
[4] Suitable chelants are, for example, diethylenetetraamine pentaacetic acid (DTPA) supplied by Dow Chemical, Midland, Michigan, USA or Hydroxyethane di phosphonate (HEDP) supplied by Solutia, St Louis, Missouri, USA Bagsvaerd, Denmark
[5] Natalase ®, Mannaway ® are all products of Novozymes, Bagsvaerd, Denmark.
6. Proteases may be supplied by Genencor International, Palo Alto, California, USA (e.g. Purafect Prime ®) or by Novozymes, Bagsvaerd, Denmark (e.g. Liquanase ®, Coronase ®).
[10] Suitable Fluorescent Whitening Agents are for example, Tinopal ® AMS, Tinopal ® CBS-X, Sulphonated zinc phthalocyanine Ciba Specialty Chemicals, Basel, Switzerland
[11] Alkoxylated Esteramine as prepared in any of Synthesis Examples 1-4
[12] Amphiphilic alkoxylated grease cleaning polymer is a polyethyleneimine (MW = 600) with 24 ethoxylate groups per —NH and 16 propoxylate groups per —NH.
[13] Huntsman, Salt Lake City, Utah, USA.
[14] Novozymes A/S, Bagsvaerd, Denmark.
[15] Novozymes A/S, Bagsvaerd, Denmark.

Formulation Example 2. Powdered Detergent Laundry Detergent Compositions

TABLE 7

|  | 4 (wt %) |
|---|---|
| Linear alkylbenzenesulfonate[1] | 8.2 |
| AE3S[2] | 1.9 |
| Zeolite A[3] | 1.8 |
| Citric Acid | 1.5 |
| Sodium Carbonate[5] | 29.7 |
| Silicate 1.6R ($SiO_2$:$Na_2O$)[4] | 3.4 |
| Soil release agent[6] | 0.2 |
| Acrylic Acid/Maleic Acid Copolymer[7] | 2.2 |
| Carboxymethylcellulose | 0.9 |
| Protease - Purafect ® (84 mg active/g)[9] | 0.08 |
| Amylase - Stainzyme Plus ® (20 mg active/g)[8] | 0.16 |
| Lipase - Lipex ® (18.00 mg active/g)[8] | 0.24 |
| Cellulase - Celluclean ™ (15.6 mg active/g)[8] | 0.1 |
| Esteramine according to the present disclosure[10] | 1.0 |
| TAED[11] | 3.26 |
| Percarbonate[12] | 14.1 |
| Na salt of Ethylenediamine-N,N'-disuccinic acid, (S,S) isomer (EDDS)[13] | 2.19 |
| Hydroxy ethane di phosphonate (HEDP)[14] | 0.54 |
| $MgSO_4$ | 0.38 |
| Perfume | 0.38 |
| Suds suppressor agglomerate[15] | 0.04 |
| Sulphonated zinc phthalocyanine (active)[16] | 0.0012 |
| Sulfate/Water & Miscellaneous | Balance |

[1] Linear alkylbenzenesulfonate having an average aliphatic carbon chain length $C_{11}$-$C_{12}$ supplied by Stepan, Northfield, Illinois, USA
[2] AE3S is $C_{12-15}$ alkyl ethoxy (3) sulfate supplied by Stepan, Northfield, Illinois, USA
[3] Zeolite A is supplied by Industrial Zeolite (UK) Ltd, Grays, Essex, UK
[4] 1.6R Silicate is supplied by Koma, Nestemica, Czech Republic
[5] Sodium Carbonate is supplied by Solvay, Houston, Texas, USA
[6] Soil release agent is Repel-o-tex ® PF, supplied by Rhodia, Paris, France
[7] Acrylic Acid/Maleic Acid Copolymer is molecular weight 70,000 and acrylate:maleate ratio 70:30, supplied by BASF, Ludwigshafen, Germany
[8] Savinase ®, Natalase ®, Stainzyme ®, Lipex ®, Celluclean™, Mannaway ® and Whitezyme ® are all products of Novozymes, Bagsvaerd, Denmark.
[9] Proteases may be supplied by Genencor International, Palo Alto, California, USA (e.g. Purafect Prime ®) or by Novozymes, Bagsvaerd, Denmark (e.g. Liquanase ®, Coronase ®).
[10] Alkoxylated Esteramine as prepared in any of Synthesis Examples 1-4
[11] TAED is tetraacetylethylenediamine, supplied under the Peractive ® brand name by Clariant GmbH, Sulzbach, Germany
[12] Sodium percarbonate supplied by Solvay, Houston, Texas, USA
[13] Na salt of Ethylenediamine-N,N'-disuccinic acid, (S,S) isomer (EDDS) is supplied by Octel, Ellesmere Port, UK
[14] Hydroxyethane di phosphonate (HEDP) is supplied by Dow Chemical, Midland, Michigan, USA
[15] Suds suppressor agglomerate is supplied by Dow Corning, Midland, Michigan, USA
[16] Fluorescent Brightener 1 is Tinopal ® AMS, Fluorescent Brightener 2 is Tinopal ® CBS-X, Sulphonated zinc phthalocyanine and Direct Violet 9 is Pergasol ® Violet BN-Z all supplied by Ciba Specialty Chemicals, Basel, Switzerland Formulation Example 3. Powdered Laundry Additive

TABLE 8

| Ingredients | 5 (wt %) |
|---|---|
| Sodium percarbonate[5] | 33.0 |
| Tetraacetyl ethylene diamine[4] | 10.0 |
| nonanoyloxybenzene sulphonate[7] | 7.5 |
| Esteramine[3] | 4.0 |
| C12-C16 Alkylbenzene sulphonic acid | 1.2 |
| C14-C15 alkyl 7-ethoxylate[6] | 0.25 |
| Mannanase[1] | 0.2 |
| Cellulase[2] | 0.2 |
| Brightener[8] | 0.1 |
| Sodium sulphate | Balance |

[1] Mannaway, from Novozymes (Denmark), 4 mg active enzyme per gram.
[2] Celluclean, from Novozymes (Denmark), 15.6 mg active enzyme per gram.
[3] Alkoxylated Esteramine as prepared in any of Synthesis Examples 1-4
[4] TAED is tetraacetylethylenediamine, supplied under the Peractive ® brand name by Clariant GmbH, Sulzbach, Germany
[5] Sodium percarbonate supplied by Solvay, Houston, Texas, USA
[6] AE7 is $C_{14-15}$ alcohol ethoxylate, with an average degree of ethoxylation of 7, supplied by Huntsman, Salt Lake City, Utah, USA
[7] NOBS is sodium nonanoyloxybenzenesulfonate, supplied by Future Fuels, Batesville, Arkansas, USA
[8] Suitable Fluorescent Whitening Agents are for example, Tinopal ® AMS, Tinopal ® CBS-X, Sulphonated zinc phthalocyanine Ciba Specialty Chemicals, Basel, Switzerland Formulation Example 4. Soluble Unit Dose Detergent Compositions The following composition may be encapsulated in water-soluble film, such as polyvinyl alcohol-based films (e.g., M8630 film, available from MonoSol, LLC) to form a unit dose article.

TABLE 9

| Ingredient | 6% |
|---|---|
| Anionic Surfactant HF LAS[1] | 18.2 |
| C14-15 alkyl ethoxy (2.5) sulfate | 8.73 |
| C14-15 alkyl ethoxy (3.0) sulfate | 0.87 |

TABLE 9-continued

| Ingredient | 6% |
|---|---|
| Nonionic Surfactant C24-9[2] | 15.5 |
| TC Fatty acid[15] | 6.0 |
| Citric Acid | 0.6 |
| FN3 protease[3] | 0.027 |
| FNA protease[4] | 0.071 |
| Natalase[5] | 0.009 |
| Termamyl Ultra[6] | 0.002 |
| Mannanase[7] | 0.004 |
| PEI ethoxylate dispersant[9] | 5.9 |
| RV-base[10] | 1.5 |
| DTPA[11] | 0.6 |
| EDDS[12] | 0.5 |
| Fluorescent Whitening Agent 49 | 0.1 |
| 1,2 propylene diol | 15.3 |
| Glycerol | 4.9 |
| Monoethanolamine | 6.6 |
| NaOH | 0.1 |
| Sodium Bisulfite | 0.3 |
| Calcium Formate | 0.08 |
| Polyethylene Glycol (PEG) 4000 | 0.1 |
| Fragrance | 1.6 |
| Dyes | 0.01 |
| Esteramine[14] | 1.0 |
| Water | TO BALANCE |
|  | 100% |

[1]Linear Alkyl Benzene Sasol, Lake Charles, LA
[2]AE9 is C12-13 alcohol ethoxylate, with an average degree of ethoxylation of 9, supplied by Huntsman, Salt Lake City, Utah, USA
[3]Protease supplied by Genencor International, Palo Alto, California, USA (e.g. Purafect Prime ®)
[4] Protease supplied by Genencor International, Palo Alto, California, USA
[5]Natalase ® supplied by Novozymes, Bagsvaerd, Denmark
[6]Termamyl Ultra supplied by Novozymes, Bagsvaerd, Denmark
[7] Mannanase ® supplied by Novozymes, Bagsvaerd, Denmark
8. Whitezyme supplied by Novozymes, Bagsvaerd, Denmark
[9]Polyethyleneimine (MW = 600) with 20 ethoxylate groups per —NH
[10]Sokalan 101 Polyethyleneglycol-Polyvinylacetate copolymer dispersant supplied by BASF
[11]Suitable chelants are, for example, diethylenetetraamine pentaacetic acid (DTPA) supplied by Dow Chemical, Midland, Michigan, USA
[12]Ethylenediaminedisuccinic acid supplied by Innospec Englewood, Colorado, USA
13. Suitable Fluorescent Whitening Agents are for example, Tinopal ® AMS, Tinopal ® CBS-X, Sulphonated zinc phthalocyanine Ciba Specialty Chemicals, Basel, Switzerland
[14]Alkoxylated Esteramine as prepared in any of Synthesis Examples 1-4
[15]Topped Coconut Fatty Acid Twin Rivers Technologies Quincy Massachusetts The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleaning composition comprising:
   from about 1% to about 70%, by weight of the composition, of a surfactant system, and
   from about 0.1% to about 10% of an esteramine according to Formula (I) and/or a salt thereof, (Formula I)

wherein independently from each other
   n being an integer from 0 to 12,
   m being an integer for each repetition unit n independently selected from 0 to 12;
   p being an integer from 0 to 12,
   o being an integer for each repetition unit p independently selected from 0 to 12;
   r being an integer from 0 to 12,
   q being an integer for each repetition unit r independently selected from 0 to 12;
   s being an integer from 0 to 100;
   t being an integer from 1 to 100;
   u being an integer from 0 to 100;
   v being an integer from 0 to 100;
   with the sum of s, t, u, and v being equal to or greater than 1;
   $A_1$, $A_2$, $A_3$, and $A_4$ are independently from each other and independently for each repetition units, t, u, or v, selected from the list consisting of ethyleneoxy group, propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein when s, t, u, and/or v equal to or greater than 1, the oxygen atom of the first $A_1$, $A_2$, $A_3$, and $A_4$ group is bound to the B group and the subsequent $A_1$, $A_2$, $A_3$, and $A_4$ groups, when they exist, are bound via an oxygen atom to the previous $A_1$, $A_2$, $A_3$, and $A_4$ group;
   $B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups;
   $R_4$, $R_8$, and $R_{12}$ being selected from the group consisting of H, linear alkyl, branched alkyl, and cycloalkyl;
   $R_1$, $R_2$, and $R_3$ being independently for each repetition unit o of each repetition unit p being selected from the group consisting of H, linear alkyl, branched alkyl, and cycloalkyl;

$R_5$, $R_6$, and $R_7$ being independently for each repetition unit m of each repetition unit n being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

$Z_1$, $Z_2$, $Z_3$, and/or $Z_4$, if present, being independently selected from the group consisting of —OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *,

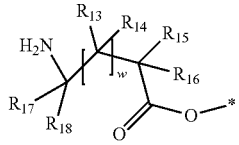

(Formula II)

with independently from each other w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl, with the proviso that at least one of $Z_1$, $Z_2$, $Z_3$, and/or $Z_4$ is present and is not —OH.

2. A cleaning composition according to claim 1, wherein n, p, and r are each equal to zero, and $Z_1$ is selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the proviso of at least one group $R_4$, $R_8$, and/or $R_{12}$ containing at least 7 or more carbon atoms;

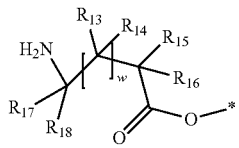

(Formula II)

with independently from each other w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

3. A cleaning composition according to claim 1, wherein p and r are both equal to 0, n is at least 1, and $Z_1$ and $Z_2$, are independently selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II),

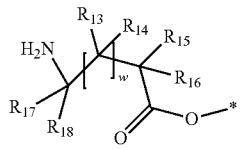

(Formula II)

with independently from each other w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl, wherein said compound according to Formula (II) connects to the compound according to Formula (I) via the bond labeled with *, with the proviso that at least one substituent $Z_1$ and/or $Z_2$ is not OH, and with the proviso that $R_3$ contains equal to or more than 2 carbon atoms.

4. A cleaning composition according to claim 1, wherein n and p are individually equal to or greater than 1, r is equal to or greater than 0, and $Z_1$, and/or $Z_2$, and/or $Z_3$, and/or $Z_4$, independently for each repetition unit n, p, and r, are selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II),

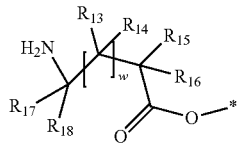

(Formula II)

with independently from each other w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl, wherein said compound according to Formula (II) connects to the compound according to Formula (I)

via the bond labeled with *, with the proviso that at least one substituent $Z_1$, and/or $Z_2$, and/or $Z_3$, and/or $Z_4$, is not OH, and wherein if n and p equal to 1 and r equal to 0 at least one unit $A_1$, $A_2$, or $A_3$ is selected from the group consisting of propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group.

5. A cleaning composition according to claim 1, wherein the composition comprises a salt of the esteramine according to claim 1, wherein the salt is formed by at least partial protonation of the amine group by an acid being a protic organic or inorganic acid.

6. A cleaning composition according to claim 1, wherein the composition comprises a salt of the esteramine according to claim 1, wherein the salt is formed by at least partial protonation of the amine group by an acid being selected from the group consisting of methanesulfonic acid, hydrochloric acid, hydrobromic acid, sulfuric acid, phosphoric acid, toluene sulfonic acid, citric acid, lactic acid, C12-C18 fatty acid, alkyl benzene sulfonic acids, alkyl sulphonic acids, alkyl sulfate acids, alkyl ethyoxysulfate acids, alkoxylated or non-alkoxylated copolymers of acrylic acid and maleic acid, and mixtures thereof.

7. A cleaning composition according to claim 1, wherein $A_1$, $A_2$, $A_3$, and $A_4$ are, independently from each other and independently for each repetition unit s, t, u, and/or v, selected from the list consisting of ethyleneoxy group, propyleneoxy group, and 1,2-butyleneoxy group.

8. A cleaning composition according to claim 1, wherein p, r, and n are all equal to 0, $Z_1$ is selected from the group consisting of alanine, glycine, lysine, and a compound according to Formula (II), wherein w is an integer in the range of from 1 to 4, and wherein the compound according to Formula (II) connects to the compound according to Formula (I) via the bond labeled with *, with the proviso of at least one group $R_4$, $R_8$, and/or $R_{12}$ containing at least 7 or more carbon atoms.

9. A cleaning composition according to claim 1, wherein p and r are both equal to 0, and n being at least 1, $Z_1$ and $Z_2$, are independently selected from the group consisting of OH, alanine, glycine, lysine, and a compound according to Formula (II), wherein w is an integer in the range of from 1 to 4, wherein the compound according to Formula (II) connects to the compound according to Formula (I) via the bond labeled with *, with the proviso that at least one substituent $Z_1$ and/or $Z_2$ is not OH, and with the proviso that $R_3$ contains equal to or more than 2 carbon atoms.

10. A cleaning composition according to claim 1, wherein p and r are both equal to 0, and n being at least 1, wherein m is equal to 1 and $R_1$ and $R_2$ are both linear $C_2$ to $C_4$ alkyl groups.

11. A cleaning composition according to claim 1, wherein when n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of OH, alanine, glycine, lysine, and a compound according to Formula (II), wherein w is an integer in the range of from 1 to 4, wherein the compound according to Formula (II) connects to the compound according to Formula (I) via the bond labeled with *, with the provisio that at least one substituent $Z_1$, and/or $Z_2$, and/or $Z_3$, and/or $Z_4$, is not OH.

12. A cleaning composition according to claim 1, wherein n and p are both equal to 1, r is equal to 0, m and o are both equal to 0, B 1 is equal to a chemical bond, $R_3$, $R_4$, $R_7$, $R_8$, and $R_{12}$ are all equal to H.

13. A cleaning composition according to claim 1, wherein n and p are both equal to 1, r is equal to 0, m and o are both equal to 0, B 1 is equal to a methylene, $R_3$, $R_4$, $R_7$, and $R_8$ are all equal to H, and Rig is equal to ethyl.

14. A cleaning composition according to claim 1, wherein the surfactant system comprises one or more surfactants selected from anionic surfactants, cationic surfactants, nonionic surfactants, amphoteric surfactants, and mixtures thereof.

15. A cleaning composition according to claim 1, wherein the cleaning composition further comprises an adjunct cleaning additive selected from the group consisting of builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, perfumes, and mixtures thereof.

16. A cleaning composition according to claim 15, wherein the adjunct cleaning additive comprises an enzyme selected from the group consisting of protease, amylase, lipase, and combinations thereof.

17. A method of pretreating or treating a soiled fabric, the method comprising the step of contacting the soiled fabric with the cleaning composition of claim 1, optionally wherein the soiled fabric comprises a greasy stain.

18. A cleaning composition comprising:
from about 1% to about 70%, by weight of the composition, of a surfactant system, and
from about 0.1% to about 10% of an esteramine, and/or salt thereof, obtainable by:
a) reacting an alcohol according to Formula (III)

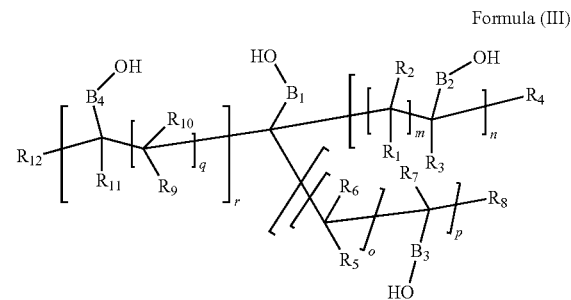

Formula (III)

wherein independently from each other
n being an integer from 0 to 12,
m being an integer for each repetition unit n independently selected from 0 to 12;
p being an integer from 0 to 12,
o being an integer for each repetition unit p independently selected from 0 to 12;
r being an integer from 0 to 12,
q being an integer for each repetition unit r independently selected from 0 to 12;
$B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$R_1$, $R_2$, and $R_3$ being independently for each repetition unit o of each repetition unit p being selected from the group consisting of H, linear alkyl, branched alkyl, and cycloalkyl;

$R_5$, $R_6$, and $R_7$ being independently for each repetition unit m of each repetition unit n being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

with one or more $C_2$ to $C_{16}$ alkylene oxide, followed by b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof;

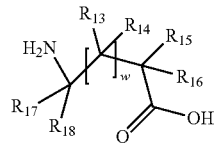

(Formula IV)

with w being an integer from 0 to 12, $R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

19. A cleaning composition according to claim 18, wherein the molar ratio of alcohol according to Formula (III) to total $C_2$ to $C_{12}$ alkylene oxide is in the range of from 1:1 to 1:400.

20. A cleaning composition according to claim 18, wherein the molar ratio of the acid to the hydroxyl groups of the alkoxylated alcohol is in the range of from 0.1:1 to 1:1.

* * * * *